United States Patent [19]
Kitada et al.

[11] Patent Number: 5,925,731
[45] Date of Patent: Jul. 20, 1999

[54] ENDOTHELIN ANTAGONIST PEPTIDES

[75] Inventors: Chieko Kitada, Osaka; Taiji Asami; Tetsuya Ohtaki, both of Ibaraki; Toshifumi Watanabe, Osaka, all of Japan

[73] Assignee: Takeda Chemical Industries, Ltd., Osaka, Japan

[21] Appl. No.: 08/732,289

[22] PCT Filed: Sep. 26, 1996

[86] PCT No.: PCT/JP96/02778

§ 371 Date: Oct. 28, 1996

§ 102(e) Date: Oct. 28, 1996

[87] PCT Pub. No.: WO97/11961

PCT Pub. Date: Mar. 3, 1997

[30] Foreign Application Priority Data

Sep. 26, 1995 [JP] Japan .................................... 7-248176
Nov. 17, 1995 [JP] Japan .................................... 7-300336

[51] Int. Cl.⁶ .................................................. A61K 38/07
[52] U.S. Cl. ............................ 530/330; 530/331; 514/16; 514/17; 514/18
[58] Field of Search ....................... 514/16–18; 530/330, 530/331

[56] References Cited

U.S. PATENT DOCUMENTS 5,268,360 12/1993 Yoshikawa ................................ 514/18
5,688,913 11/1997 Arrhenius ................................ 530/330

FOREIGN PATENT DOCUMENTS 0 457 195 A2 11/1991 European Pat. Off. .
0 552 489 A2 7/1993 European Pat. Off. .
0 555 537 8/1993 European Pat. Off. .
WO96/11927 4/1996 WIPO .

OTHER PUBLICATIONS

T. Fukami et al., *Bioorganic & Medicinal Chemistry Letters*, 5(14), 1483–1488 (1995).

*Primary Examiner*—Cecilia J. Tsang
*Assistant Examiner*—David Lukton
*Attorney, Agent, or Firm*—Wenderoth, Lind & Ponack, LLP

[57] ABSTRACT

The peptide derivatives having endothelin receptor-antagonistic action or a salt thereof and medicinal compositions containing them are provided.

Since peptide derivatives or a salt thereof of this invention exhibit remarkable endothelin receptor-antagonistic action with low toxicity, they are effective as medicines for prophylaxis and therapy of, for example, cardio- or cerebro-circulatory diseases hepatic diseases and/or renal diseases.

23 Claims, No Drawings

ENDOTHELIN ANTAGONIST PEPTIDES

This application is a 371 national stage application of International Application No. PCT/JP96/02778 filed Sep. 26, 1996.

BACKGROUND OF THE INVENTION

1. Field of the Invention

This invention relates to a novel peptide derivative, exhibiting endothelin receptor antagonistic action, which is pharmaceutically useful as, for example, a therapeutic or prophylactic agent of cardio- or cerebro-circulatory disease, hepatic disease and/or renal disease, a method of producing it, and a pharmaceutical composition containing the compound.

2. Description of Related Art

Endothelin (ET) is a vasoconstricting peptide consisting of 21 amino acids, which was isolated from the supernatant of swine arterial endothelial culture and structurally determined by Yanagisawa et al. [Yanagisawa et al.: Nature, Vol. 332, pp.411–415 (1988)]. Endothelin was later found to exhibit a variety of actions, and endothelin antibodies as endothelin antagonists have proven effective in the treatment of myocardial infarction, renal failure and other diseases. Since endothelin is present in living bodies and exhibits vasoconstricting action, it is be an endogenous factor involved in the regulation of the circulatory system and has an association with hypertension, cardio- or cerebrovascular diseases, e.g. myocardial infarction: and renal diseases, e.g. acute renal failure: and hepatic diseases, e.g. hepatargia. Since it also exhibits bronchial smooth muscle constricting action, it has an association with asthma.

While, as endothelin antagonists, there have recently been disclosed peptides exhibiting endothelin antagonistic action in JP-A 107680/1994 and Bioorganic & Medicinal Chemistry Letters, Vol. 5, pp.1483 (1995), those exhibiting actions are not sufficient.

SUMMARY OF THE INVENTION

Circumstances being such as above, the present inventors have studied intensively. As a result, the inventors found that a peptide derivative whose C-terminal is an amino acid reside which is amidated with an optionally substituted heterocyclic group and is substituted with a carboxyl group or an heterocyclic group capable of releasing proton, or a salt thereof, exhibits excellent endothelin receptor antagonistic action.

Namely, the present invention relates to:

(1) a peptide derivative, whose C-terminal is the amino acid residue which is amidated with an optionally substituted heterocyclic group, and is substituted with a carboxyl group or a heterocyclic group capable of releasing proton, or a salt thereof, (2) a peptide derivative, wherein one carboxyl group on the amino acid residue at C-terminal is amidated with an optionally substituted heterocyclic group, and the hydrogen atom on a carbon atom in the amino acid residue at C-terminal is substituted with a carboxyl group or a heterocyclic group capable of releasing proton, or a salt thereof, (3) the peptide derivative as described in (1) or (2) above, wherein the N-terminal is acylated, (4) the peptide derivative as described in (3) above, wherein the peptide derivative is acylated by an acyl group represented by the formula $R^1$—CO—, wherein $R^1$ is an optionally substituted hydrocarbon residue or an optionally substituted hydrocarbonoxy group, or a group represented by the formula $R^2R^3N$—CO—, wherein $R^2$ is an optionally substituted hydrocarbon residue or a heterocyclic group, $R^3$ is a hydrogen atom or an optionally substituted hydrocarbon residue, or $R^2$ and $R^3$ are combined with each other to form, taken together with the adjacent nitrogen atom, an N-containing saturated heterocyclic ring, (5) the peptide derivative as described in (1) or (2) above, consisting of 3 to 6 amino acid residues, (6) the peptide derivative as described in (1) or (2) above, wherein the heterocyclic group capable of releasing proton is a 4- to 6-membered heterocyclic group having 1 to 4 nitrogen atom, oxygen atom or/and sulfur atom, and optionally having a hydroxy or oxo group as the substituent, or the heterocyclic-group which is condensed with a benzene-ring, (7) the peptide derivative as described in (1) or (2) above, wherein the substituent of the optionally substituted heterocyclic group is a $C_{1-6}$ alkyl group, an optionally substituted $C_{6-14}$ aryl group, a N-containing 5- to 6-membered heterocyclic group, a halogen atom, nitro, cyano, hydroxy, a $C_{1-6}$ alkoxy group, amino, oxo, amidino, imino, mercapto, sulfo, a mono- or di-$C_{1-6}$ alkylamino, formylamino, a $C_{1-6}$ alkylsulfonylamino group, a $C_{1-6}$ alkoxycarbonyl group, carboxyl, formyl, a $C_{1-6}$ alkylcarbonyl group, a $C_{2-6}$ alkenyl group, a $C_{2-6}$ alkynyl group, a $C_{3-9}$ cycloalkyl group, a $C_{5-7}$ cycloalkenyl group, a $C_{7-13}$ aralkyl group, a $C_{1-6}$ alkylthio group, a $C_{1-6}$ alkylsulfinyl group, a $C_{1-6}$ alkylsulfonyl group, or a group of the formula: $R^9$—CO—$X^3$—, wherein $R^9$ is a $C_{1-6}$ alkyl group, a $C_{1-6}$ alkoxy group, or an amino group which may optionally be substituted with $C_{1-6}$ alkyl, and $X^3$ is an oxygen atom or a group of the formula: —$NR^{10}$—, wherein $R^{10}$ is a hydrogen atom or a $C_{1-6}$ alkyl group, (8) the peptide derivative as described in (1) or (2) above, wherein the heterocyclic group of the optionally substituted heterocyclic group is a 5- to 8-membered heterocyclic group containing 1 to 3 nitrogen atoms and optionally containing oxygen atom or/and sulfur atom, which is a N-containing heterocyclic group having a chemical bond at the ring-constituting nitrogen atom or its dicyclic or tricyclic condensed heterocyclic group, (9) the peptide derivative as described in (1) or (2) above, wherein the amino acid residue of the C-terminal is Asp, Glu, tetrazolyl-α-Ala or tetrazolyl-β-Ala wherein one carboxyl group of the amino acid residue is amidated with an optionally substituted heterocyclic group,

(10) the peptide derivative as described in (9) above, wherein Asp or Glu is of D-configuration,

(11) the peptide derivative as described in (1) or (2) above, which is represented by the formula, $R^{1'}$—CO—$A_1$—$A_2$—$A_3$—$A_4$, wherein $R^{1'}$ is an optionally substituted N-containing saturated heterocyclic group having a chemical bond at the ring-consituting nitrogen atom, $A_1$ is Leu, Ile or Nle, $A_2$ is an optionally substituted D-Trp, $A_3$ is D-Leu, D-Ile or D-Nle, and $A_4$ is Asp, Glu, tetrazolyl-α-Ala or tetrazolyl-β-Ala wherein one carboxyl group is amidated with an optionally substituted heterocyclic group,

(12) the peptide derivative as described in (11) above, wherein the substituent of the optionally substituted N-containing saturated heterocyclic group for $R^{1'}$ is a $C_{1-6}$ alkyl group, phenyl, a halogen atom, nitro, cyano, hydroxy, oxo, a $C_{1-6}$ alkoxy group, amino or a mono- or di-$C_{1-6}$ alkylamino group,

(13) the peptide derivative as described in (11) above, wherein the substituent of D-Trp is a $C_{1-6}$ alkyl group, a $C_{1-6}$ alkoxy group, a $C_{1-6}$ alkoxy-carbonyl group, a $C_{1-6}$ acyl group, cyano, a halogen atom, hydroxy, a hydroxy-$C_{1-6}$ alkyl group or a group of the formula: —S(O)$_a$—R$^{21}$, wherein a is an integer of 0 to 2, R$^{21}$ is a $C_{1-6}$ alkyl group,

(14) the peptide derivative as described in (11) above, wherein the substituent of the heterocyclic group for $A_4$ is a $C_{6-14}$ aryl group,

(15) the peptide derivative as described in (1) or (2) above, which is hexamethyleniminocarbonyl-Leu-D-Trp(COOMe)-D-Nle-D-Asp (2MeOPhp),

(16) the peptide derivative as described in (1) or (2) above, which is hexamethyleniminocarbonyl-Leu-D-Trp(COOMe)-D-Nle-Atp-2MeOPhp,

(17) A method of producing a peptide derivative or a salt thereof, wherein the C-terminal is the amino acid residue amidated with an optionally substituted heterocyclic group, and substituted with carboxyl group, which comprises subjecting a peptide derivative whose C-terminal is the amino acid residue amidated with an optionally substituted heterocyclic group, and substituted with a protected carboxyl group to an elimination reaction of the protective group,

(18) A method of producing a peptide derivative or a salt thereof, wherein the C-terminal is the amino acid residue amidated with an optionally substituted heterocyclic group, and substituted with a heterocyclic group capable of releasing proton, and N-terminal is acylated, which comprises subjecting a peptide whose C-terminal is the amino acid residue amidated with an optionally substituted heterocyclic group, and substituted with a heterocyclic group capable of releasing proton, and a peptide whose N-terminal is acylated to a condensation reaction,

(19) a pharmaceutical composition containing the peptide derivative described in (1) or (2) above, or a pharmaceutically acceptable salt thereof,

(20) the pharmaceutical composition described in (19) above, which is an endothelin receptor antagonist,

(21) the pharmaceutical composition as described in (20) above, in which the endothelin receptor antagonist is a therapeutic or prophylactic agent of cardio- or cerebrocirculatory disease, hepatic disease and/or renal disease,

(22) the pharmaceutical composition as described in (20) above, in which the endothelin receptor antagonist is a vasoconstriction inhibitor of cardio- or cerebrovascular, hepatic vascular and/or renal vascular,

(23) the pharmaceutical composition described in (20) above, in which the endothelin receptor antagonist is a therapeutic or prophylactic agent of acute renal failure, myocardial infarction, and/or bronchial,

(24) a therapeutic method of acute renal failure, myocardial infarction or bronchial comprising administering an effective amount of the pharmaceutical composition claimed in (19) above, to the mammal suffering from acute renal failure, myocardial infarction or bronchial disease,

(25) use of the peptide derivative as described in (1) or (2) above, for the manufacture of an endothelin antagonistic composition.

More specifically, the following inventions are mentioned.

(26) The peptide derivative described in (1) or (2) above, which consists of 3 or 4 amino acid residues.

(27) The peptide derivative described in (1) or (2) above, which consists of 4 amino acid residues.

(28) The peptide derivative described in (4) above, wherein one or two methylene group of a $C_{4-8}$ 5- to 9-membered N-containing saturated heterocyclic ring which is formed by the combination of $R^2$ and $R^3$ with the adjacent nitrogen atom, may optionally be substituted with one or two oxygen atom and/or sulfur atom, and the saturated heterocyclic group may optionally be condensed with a benzene ring on adjacent two carbon atoms in the said heterocyclic ring.

(29) The peptide derivative described in (1) or (2) above, which is represented by the formula;
X—B—CH($R^4$)—C(=O)—$X^1$—CH($R^5$)—C(=$X^2$)—NH—CH($R^6$)—(CH$_2$)n—C(=O)—Y, wherein X is a group of the formula $R^1$—CO—, wherein $R^1$ is of the same meaning as defined above, or the formula $R^2R^3$N—CO—, wherein $R^2$ or $R^3$ is of the same meaning as defined above, B is an oxygen atom or a group of the formula —NR$^7$—, wherein $R^7$ is a hydrogen atom or a hydrocarbon residue, $R^4$ is a hydrocarbon residue or a heterocyclic group, $X^1$ is an oxygen atom or a group of the formula —NR$^8$—, wherein $R^8$ is a hydrogen atom or a hydrocarbon residue, $R^5$ is an optionally substituted heterocyclic-alkyl group, $X^2$ is an oxygen atom or a sulfur atom, $R^6$ is an optionally substituted hydrocarbon residue, n is 0 or 1, Y is an amino acid residue which is substituted with a carboxyl group or a heterocyclic group capable of releasing proton and wherein one carboxyl group on the amino acid residue is amidated with an optionally substituted N-containing heterocyclic group.

(30) The peptide derivative described in (4) above, in which the N-containing saturated heterocyclic group of the formula $R^2R^3$N— is 5- to 9-membered heterocyclic.

(31) The peptide derivative described in (4) above, wherein the N-containing saturated heterocyclic group of the formula $R^2R^3$N— may optionally contain further one or two oxygen atom or sulfur atom.

(32) The peptide derivative described in (1) or (2) above, which is represented by the formula X—$A_{11}$—$A_{12}$—$A_{13}$—Y, wherein X is an acyl group, $A_{11}$, $A_{12}$ and $A_{13}$ are optionally substituted amino acid residues, Y is an amino acid residue which is substituted with a carboxyl group or a heterocyclic group capable of releasing proton and wherein one carboxyl group on the amino acid residue is amidated with an optionally substituted heterocyclic group.

(33) The peptide derivative described in (11) above, wherein $A_1$ is Leu.

(34) The peptide derivative described in (11) above, wherein $A_2$ is D-Trp substituted with $C_{1-6}$ alkoxycarbonyl.

(35) The peptide derivative described in (11) above, wherein $A_3$ is D-Nle.

(36) The peptide derivative described in (11) above, wherein $A_4$ is Asp or Glu which is substituted with a 5-or 6-membered heterocyclic group containing 1 to 4 nitrogen atoms, and said heterocyclic group is substituted with $C_{6-14}$ aryl which may optionally have a halogen atom or a $C_{1-6}$ alkoxy group.

(37) The peptide derivative described in (11) above, wherein $A_4$ is Asp which is substituted with a 5- or 6-membered heterocyclic group containing 1 to 4 nitrogen atoms, and said heterocyclic group is substituted with a $C_{6-14}$ aryl group having a $C_{1-6}$ alkoxy group.

(38) The peptide derivative described in (11) above, wherein $A_4$ is tetrazolyl-α-Ala or tetrazolyl-β-Ala which is amidated with a 5- to 6-membered heterocyclic group containing 1 to 4 nitrogen atoms, and said heterocyclic group is substituted with a $C_{6-14}$ aryl group having a $C_{1-6}$ alkoxy group.

DETAILED DESCRIPTION OF PREFERRED EMBODIMENT(S)

In this application, when an amino acid is represented by the formula $H_2NCHR^0COOH$, wherein $R^0$ is an optional substituent, an amino acid residue is represented by the formula —$NHCHR^0CO$—, and the structure is formed by losing $H_2O$ molecules and generating peptide bond, and then joining to a protein or a peptide at a position except C- or N-terminal. Also in this application, an amino acid residue at N-terminal is represented by the formula $H_2NCHR^0CO$—, and an amino acid residue at C-terminal is represented by the formula —$NHCHR^0COOH$.

The above-mentioned heterocyclic group capable of releasing proton includes a 4- to 6-membered heterocyclic group having 1 to 4 nitrogen atom, oxygen atom and/or sulfur atom, which may optionally have a hydroxy group or an oxo group as the substituent, which is specifically exemplified by tetrazolyl, 3-oxo-1,2,4-triazolyl, 5-oxo-1,2,4-oxadiazolyl, 3-hydroxyisoxazolyl, 3-oxo-1,2,4-oxadiazolyl, 3,5-dioxo-1,2,4-oxadiazolidinyl, 2-oxo-3H-1,2,3,5-oxathiadiazolyl, 5-oxoisoxazolyl, 2-oxo-1,3,4-oxadiazolyl, 1-oxo-5H-1,2,3,4-thiatriazolyl, and 1,1-dioxo-2H-benzo[e][1,2,4]thiadiazinyl.

Among them, more preferable examples of the heterocyclic group capable of releasing proton include tetrazolyl (preferably 1H-tetrazol-5-yl), 3-oxo-1,2,4-oxadiazolyl, 5-oxo-1,2,4-oxadiazolyl and 2-oxo-1,3,4-oxadiazolyl.

The heterocyclic group in the above-mentioned optionally substituted heterocyclic group includes a 5-to 8-membered heterocyclic group containing 1 to 3 nitrogen atoms and optionally containing hetero-atoms such as an oxygen atom and/or a sulfur atom, and which is a N-containing heterocyclic group having a chemical bond at the ring-constituting nitrogen atom or its dicyclic or tricyclic condensed heterocyclic group. Examples of the N-containing heterocyclic group include 1-pyrrolidinyl, 1-piperidyl, 1-piperazinyl, 4-morpholinyl, hexamethylenimino, heptamethylenimino, 4-oxazolin-3-yl, thiazolidin-3-yl, 4-thiomorpholinyl, 1-imidazolidinyl, 1-pyrrolinyl, 1,2-dihydropyridin-1-yl, 1,4-dihydropyridin-1-yl, 1,2,3,6-tetrahydropyridin-1-yl, 2-oxazolidinyl, 1-imidazolyl, 1-pyrazolyl, 1,4,5,6-tetrahydropyrimidin-3-yl, 1-pyrrolyl, 2-imidazolin-1-yl, 1-pyrazolidinyl, 3-pyrazolin-1-yl, 3-pyrazolin-2-yl, 1,2,4-triazol-1-yl, 1-tetrazolyl, ortho-oxadin-2-yl, para-oxadin-4-yl, 2H-1,2-thiazin-2-yl, 4H-1,4-thiazin-4-yl, 3-thiazolinyl, 1,3,4-thiadiazolidin-3-yl, 1,3,4-thiadiazolin-3-yl, 4H-1,3,4-thiadiadin-4-yl.

Examples of the dicyclic or tricyclic condensed heterocyclic group include 2,3-dihydro-1H-indolin-1-yl, 1,2,3,4-tetrahydroquinolin-1-yl, 2,3,4,5-tetrahydro-1H-1-benzazepinyl, 2,3-dihydro-1H-isoindolin-2-yl, 1,2,3,4-tetrahydroisoquinolin-2-yl, 2,3,4,5-tetrahydro-1H-2-benzazepinyl, 2,3,4,5-tetrahydro-1H-3-benzazepinyl, 1,2,3,4,5,6-hexahydro-1-benzazocinyl, 1,2,3,4,5,6-hexahydro-2-benzaocinyl, 1,2,3,4,5,6-hexahydro-3-benzazocinyl, 2,3,4,5,6,7-hexahydro-1H-1-benzazonyl, 2,3,4,5,6,7-hexahydro-1H-2-benzazonyl, 2,3,4,5,6,7-hexahydro-1H-3-benzazonyl, 2,3,4,5,6,7-hexahydro-1H-4-benzazonyl, 2- or 9-(β-carbolyl), phenoxazin-10-yl, phenothiazin-10-yl, 3H-3-benzoazepinyl, 3,4-dihydroquinolin-1-yl, benzimidanyl, 1,4-benzodiazepinyl and 10,11-dihydro-5H-dibenz(b,f)azepin-5-yl.

More preferable examples of the said N-containing heterocyclic group include hexamethylenimino, 10,11-dihydro-5H-dibenz(b,f)azepin-5-yl, 4-morpholinyl, 1-piperazinyl and azepinyl.

These heterocyclic groups may optionally have 1 to 3, more preferably 1 or 2 substituents. Examples of the substituent include (1) a straight-chain or branched $C_{1-6}$ alkyl group, e.g. methyl, trifluoromethyl, ethyl, n-propyl, isopropyl, butyl, sec-butyl, tert-butyl, pentyl, isopentyl, neopentyl, tert-pentyl, 1-methylbutyl, 2-methylbutyl, 1,2-dimethylpropyl, 1-ethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methyl, (2) an optionally substituted $C_{6-14}$ aryl group, e.g. phenyl, tolyl, xylyl, naphthyl and anthracenyl, (3) a N-containing 5- to 6-membered heterocyclic group, e.g. pyrrolyl, pyrazolyl, pyrrolidinyl, imidazolyl, imidazolidinyl, pyridyl, pyrimidyl, pyridazinyl, piperidinyl and piperazinyl, (4) a halogen atom, e.g. fluorine, chlorine, bromine and iodine, (5) nitro, (6) cyano, (7) hydroxy, (8) a $C_{1-6}$ alkoxy group, e.g. methoxy, ethoxy, n-propoxy, isopropoxy, n-butoxy, isobutoxy, sec-butoxy and tert-butoxy, (9) amino, (10) oxo, (11) amidino, (12) imino, (13) mercapto, (14) sulfo, (15) a mono- or di-$C_{1-6}$ alkylamino group, e.g. methylamino, ethylamino, propylamino, dimethylamino and diethylamino, (16) formylamino, (17) a $C_{1-6}$ alkylsulfonylamino group, e.g. methylsulfonylamino, ethylsulfonylamino and propylsulfonylamino, (18) a $C_{1-6}$ alkoxycarbonyl group, e.g. methoxycarbonyl, ethoxycarbonyl, propoxycarbonyl and butoxycarbonyl, (19) carboxyl, (20) formyl, (21) a $C_{1-6}$ alkylcarbonyl group, e.g. acetyl, propionyl, butanoyl, pentanoyl, (22) a $C_{2-6}$ alkenyl group, e.g. vinyl, 1-methylvinyl, 1-propenyl and allyl, (23) a $C_{2-6}$ alkynyl group, e.g. ethynyl, 1-propynyl and propargyl, (24) a $C_{3-9}$ cycloalkyl group, e.g. cyclopropyl, cyclobutyl, cyclopentyl, cyclohexyl, cycloheptyl, cyclooctyl and cyclononyl, (25) a $C_{5-7}$ cycloalkenyl group, e.g. cyclopentenyl and cyclohexenyl, (26) a $C_{7-13}$ aralkyl group, e.g. benzyl, α-methylbenzyl, phenethyl, phenylpropyl and benzhydryl, (27) a $C_{1-6}$ alkylthio group, e.g. methylthio, ethylthio, propylthio, isopropylthio, buthylthio and isobutylthio, (28) a $C_{1-6}$ alkylsulfinyl group, e.g. methylsulfinyl, ethylsulfinyl, propylsulfinyl, isopropylsulfinyl, butylsulfinyl and isobutylsulfinyl, (29) a $C_{1-6}$ alkylsulfonyl group, e.g. methylsulfonyl, ethylsulfonyl, propylsulfonyl, isopropylsulfonyl, butylsulfonyl and isobutylsulfonyl and (30) a group of the formula: $R^9$—CO—$X^3$—, wherein $R^9$ is a $C_{1-6}$ alkyl group (defined as above), a $C_{1-6}$ alkoxy group (defined as above), or an amino group which is optionally substituted with a $C_{1-6}$ alkyl group (defined as above), and $X^3$ is an oxygen atom or group of the formula: —$NR^{10}$—, wherein $R^{10}$ is a hydrogen atom or a $C_{1-6}$ alkyl group (defined as above), e.g. methylureido, ethylureido, acetoxy, acetamide and methylcarbamoyloxy.

Examples of the substituent of an optionally substituted $C_{6-14}$ aryl group include (1) a halogen atom, (2) nitro, (3) amino, (4) formylamino, (5) cyano, (6) hydroxy, (7) a $C_{1-6}$ alkoxy group, (8) a $C_{1-6}$ alkyl group, e.g. methyl, ethyl, n-propyl, isopropyl, butyl and t-butyl, (9) trifluoromethyl and (10) a $C_{1-6}$ alkylthio group. Among these substituents, a halogen atom or a $C_{1-6}$ alkoxy group is especially preferable.

The substituent of the heterocyclic group as mentioned above is preferably a $C_{6-14}$ aryl group or a 5- or 6-membered N-containing heterocyclic group.

The number of the substituents is 1 to 3, preferably 1 to 2.

The N-terminal of the peptide is preferably acylated by the acyl group. The acyl group at the N-terminal includes a group represented by the formula $R^1$—CO—, wherein $R^1$ is an optionally substituted hydrocarbon residue or an optionally substituted hydrocarboxy group, or a group represented by the formula $R^2R^3N$—CO—, wherein $R^2$ is an optionally substituted hydrocarbon residue or a heterocyclic group, $R^3$ is a hydrogen atom or an optionally substituted hydrocarbon residue, or $R^2$ and $R^3$ are combined with each other to form, taken together with the adjacent nitrogen atom, an N-containing saturated heterocyclic ring.

Examples of the hydrocarbon residue in the optionally substituted hydrocarbon residue and in the optionally substituted hydrocarbonoxy group represented by $R^1$ mentioned above include a straight-chain or branched hydrocarbon group as exemplified by a $C_{1-15}$ alkyl group, e.g. methyl, ethyl, n-propyl, isopropyl, butyl, sec-butyl, tert-butyl, pentyl, isopentyl, neopentyl, tert-pentyl, 1-methylbutyl, 2-methylbutyl, 1,2-dimethylpropyl, 1-ethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl, 1-ethyl-1-methyl, heptyl, octyl, nonyl, decyl, undecyl, dodecyl, tridecyl, tetradecyl and pentadecyl, a $C_{2-10}$ alkenyl group, e.g. vinyl, allyl, 2-methylallyl, 2-propenyl group, isopropenyl, 1-butenyl, 2-butenyl, 3-butenyl, 1-methyl-2-propenyl, 1-methyl-1-propenyl, 1-ethyl-1-ethenyl, 2-methyl-2-propenyl, 2-methyl-1-propenyl, 4-pentenyl, 5-pentenyl and 3-octenyl, and a $C_{2-10}$ alkynyl group, e.g. ethynyl, 2-propynyl and 3-hexynyl; cyclohydrocarbon group as exemplified by a $C_{3-9}$ cycloalkyl group, e.g. cyclopropyl, cyclobutyl, cyclopentyl, cyclohexyl, cycloheptyl, cyclooctyl and cyclononyl, a $C_{3-10}$ cycloalkenyl group, e.g. cyclopropenyl, cyclopentenyl and cyclohexenyl, a $C_{6-14}$ aryl group, e.g. phenyl, tolyl, xylyl, 1-naphthyl, 2-naphthyl, biphenylyl, anthryl, phenanthryl, azulenyl and anthracenyl and 1-adamantyl; a straight-chain or branched hydrocarbon group which is substituted with cyclohydrocarbon group as exemplified by a $C_{7-9}$ aralkyl group, e.g. benzyl, phenethyl, phenylpropyl, benzhydryl, trityl, 9-fluorenylmethyl and biphenylylisopropyl; and a straight-chain or branched hydrocarbon which is substituted with a heterocyclic group as exemplified by pyridylethyl, pyrazinylethyl, indolylethyl and quinolylethyl.

Examples of the substituent in the optionally substituted hydrocarbon residue and in the optionally substituted hydrocarboxy group of $R^1$ include the same ones of the above-mentioned substituents (3)–(21), (28)–(30) of the heterocyclic group.

The hydrocarbon residue in the optionally substituted hydrocarbon group of $R^2$ or $R^3$ in the above-mentioned formula $R^2R^3N$—CO—, include the same ones as hydrocarbon residue of the above-mentioned $R^1$, and, substituent thereon include the same ones as the substituent of the hydrocarbon residues of the above-mentioned $R^1$. The number of these substituents ranges preferably from 1 to 3, more preferably 1 or 2.

Examples of heterocyclic groups in the optionally substituted heterocyclic group of $R^2$ include a 5-membered heterocyclic group containing, besides carbon atoms, 1 to 4 hetero-atoms selected from an oxygen atom, a sulfur atom and a nitrogen atom, such as 2- or 3-thienyl, 2- or 3-furyl, 2-pyrrolin-2- or 3-yl, 3- pyrrolin-2- or 3-yl, 2- or 3-pyrrolidinyl, 2-,4- or 5-oxazolyl, 2-,4- or 5-oxazolidinyl, 2- or 3-furazanyl, 2-,3-,4- or 5-thiazolyl, 2-,4- or 5-thiazolidinyl, 1-,3-,4- or 5-pyrazolyl, 3- or 5-pyrazolidinyl, 1-,2-,4-or 5-pyrazolinyl, 1-,2-,4- or 5-imidazolyl, 2- or 4-imidazolidinyl, 1-,2-,4- or 5-imidazolinyl, 1-,3-,4- or 5-isoxazolyl, 1-,3-,4- or 5-isothiazolyl, 2-,3-,4- or 5-(1,2,4-oxadiazolyl), 2-,3-,4- or 5-(1,2,4-thiadiazolyl), 2- or 3-(1,3,4-thiadiazolyl), 2-,3-,4-or 5-(1,2,3-thiadiazolyl), 2- or 3-(1,2,5-thiadiazolyl), 1-,2-,3-, 4- or 5-(1,2,3-triazolyl), 1-,2-,3-,4- or 5-(1,2,4-triazolyl), 1-,2- or 3-(1H- or 2H-tetrazolyl), 1,2,3,5-oxathiadiazolyl and 1,2,3,4-thiatriazolyl, 2-,4- or 5-oxazolidinyl, 2-,4- or 5-thiazolidinyl; a 6- to 8-membered heterocyclic group containing, besides carbon atoms, 1 to 4 hetero-atoms selected from oxygen atom, sulfur atom and nitrogen atom, such as 1-,2-,3- or 4-pyridyl, 1-,2-,4- or 5-pyrimidinyl, 1-,3- or 4-pyridazinyl, 2- or 3-morpholinyl, 2- or 3-thiomorpholinyl, oxoimidazinyl, dioxotriazinyl, 2-or 3-piperazinyl, 2-,3- or 4-piperidyl, 3-,4-,5- or 6-pyranyl, 3-,4-,5- or 6-thiopyranyl, 2-,3-,4-,5- or 6-(1,4-oxazinyl), 2-,3-,4-,5- or 6-(1,4-thiazinyl), 2-,3-,4-,5- or 6-(1-,3-thiazinyl), 1- or 2-piperazinyl, 3- or 5-triazinyl, oxotriazinyl, 3- or 4-pyridazinyl, 2-pyrazinyl, 2-,3-,4- or 5-hexamethylenimino, 2-,3-,4- or 5-heptamethyleneimino, 3-,4-,5- or 6-(1,2-dihydropyridyl), 2-,3-,5- or 6-(1,4-dihydropyridyl), 3- or 4-(1,2,3,6-tetrahydropyridyl), 2-,3-,4- or 5-imidazolyl, 1-,3- or 4-pyrazolyl, 1-,2-,4- or 5-(1,4,5,6-tetrahydropyrimidinyl) and azepinyl; and a dicyclic or tricyclic condensed heterocyclic group containing, besides carbon atoms, 1 to 4 hetero-atoms selected from an oxygen atom, a sulfur atom and a nitrogen atom, such as 2-,3-,4-, 5-,6- or 7-benzofuranyl, 2-,3-,4-,5-,6- or 7-benzothienyl, 1-,3-,4-,5-,6-or 7-isobenzofuranyl, 2-,3-,4-,5-,6-or 7-benzothiazolyl, 2-,4-,5-,6- or 7-benzoxazolyl, 2-,4-,5-,6- or 7-benzimidazolyl, 1-,2-,4-,5-,6- or 7-tetrazolo[1,5-b]pyridazinyl, 1-,4-,5-,6- or 7-triazolo[4,5-b]pyridazinyl, 2-,3-,4-,5-,6-,7-,or 8-quinolyl, 1-,3-,4-,5-,6-,7- or 8-isoquinolyl, 3-,4-,5-, 6-,7- or 8-cinnolinyl, 1-,4-,5-,6-,7- or 8-phthalazinyl, 2-,4-,5-,6-,7- or 8-quinazolinyl, 2-,3-,5-,6-, 7- or 8-quinoxalinyl, 1-,2-,3-,5-,6-,7- or 8-indolizinyl, 2-,3-, 4-,5-,6- or 7-indolyl, 1-,3-,4-,5-,6- or 7-isoindolyl, 1-,2-,3-, 4-,6-,7-,8- or 9-quinolizinyl, 2-,3-,4-,5-,6- or 7-(1,8-naphthyridinyl), 2-,6-,7- or 8-purinyl, 2-,4-,6- or 7-pteridinyl, 1-,2-,3-,4-,5-,6- or 7-dibenzofuranyl, 1-,2-,3-, 4- or 9 -carbazolyl, 1-,2-,3-,4- or 9-acridinyl, 1-,2-,3-,4- or 6-phenanthridinyl, 1-,2-,4-,5- or 6-perimidinyl, 2-,3-,4-,5-, 6-,7- or 8-chromanyl, 2-,3-,4-,5-,6-,7- or 8-chromenyl, 2-,3-, 4-,5-,6- or 7-benzoxazinyl, 1- or 2-phenazinyl, 1-,2-,3-, or 4-phenothiazinyl, 1-,2-,3- or 4-phenoxazinyl, 1-,2-,3- or 4-xanthenyl, 1-,2-,3-,4-,5-,6-, or 7-(2,3-dihydro-1H-indolyl), 2-,3-,4-,5-,6-,7- or 8-(1,2,3,4-tetrahydroquinolyl), 2,3,4,5-tetrahydro-1H-1-benzazepinyl, 2,3-dihydro-1H-isoindolyl, 1,2,3,4-tetrahydroisoquinolyl, 2,3,4,5-tetrahydro-1H-2-benzazepinyl, 2,3,4,5-tetrahydro-1H-3-benzazepinyl, 1,2,3,4,5,6-hexahydro-1-benzazocinyl, 1,2,3, 4,5,6-hexahydro-2-benzazocinyl, 1,2,3,4,5,6-hexahydro-3-benzazocinyl, 2,3,4,5,6,7-hexahydro-1H-1-benzazonyl, 2,3, 4,5,6,7-hexahydro-1H-2-benzazonyl, 2,3,4,5,6,7-hexahydro-1H-3-benzazonyl, 2,3,4,5,6,7-hexahydro-1H-4-benzazonyl, 3-,4-,5-,6-,7-,8- or 9-(β-carbolinyl), phenothinonyl, 3H-3-benzazepinyl, 2-,3-,4-,5-,6-,7- or 8-(3, 4-dihydroquinolyl), 2-,4-,5-,6- or 7-benzimidazolinyl, 1,4-benzodiazepinyl, 10,11-dihydro-5H-dibenz(b,f)azepin-5-yl, 1-,3-,4-,5-,6-,7- or 8-isochromanyl, 2-,4-,5-,6-,7- or 8-quinazolyl and 1,2-benzodiazinyl.

Among these, hexamethylenimino, 10,11-dihydro-5H-dibenz(b,f)azepin-5-yl, 2- or 3-piperazinyl, 2-,3- or 4-piperidyl and azepinyl are especially preferable.

These heterocyclic groups may have 1 to 3, more preferably 1 or 2 substituents. Examples of the substituents include the same ones of the above-mentioned heterocyclic group.

As the N-containing saturated heterocyclic group formed by the combination of the said $R^2$ and $R^3$ taken together with the adjacent nitrogen atom, $C_{4-8}$ 5- to 9-membered N-containing saturated heterocyclic groups are preferable. They are exemplified by those formed by methylene groups taken together with the adjacent nitrogen atom, e.g. 1-pyrrolidinyl, 1-piperidyl, 1-heptamethyleneimino, 1-imidazolidinyl, 1-piperazinyl, pyrrolidin-1-yl, 1-hexamethyleneimino, 1,2-dihydropyridin-1-yl, 1,2,3,6-tetrahydropyridin-1-yl, perhydroazepin-1-yl, perhydroazocin-1-yl, perhydroazonin-1-yl, 1,3-thiazolidin-1-yl, indolin-1-yl, isoindolin-2-yl, 3-pyrrolin-1-yl, 1,5-dihydro-2H-pyrrol-1-yl, perhydro-1,4-thiazin-4-yl, 1,2,3,4-tetrahydroquinolin-1-yl, 1,2,3,4-tetrahydroisoquinolin-2-yl, 1,2,3,4-tetrahydropyridin-1-yl, 1,2,3,6-tetrahydropyridin-1-yl, perhydro-1,4-thiazepin-4-yl, 2,3,4,5-tetrahydro-1-benzazepin-1-yl, 2,3,4,5-tetrahydro-2-benzazepin-2-yl, 1,2,4,5-tetrahydro-3-benzazepin-3-yl, 2,3,4,5-tetrahydro-1H-azepin-1-yl, 2,3,6,7-tetrahydro-1H-azepin-1-yl, 1,3,4,7-tetrahydro-2H-azepin-1-yl, perhydro-1,4-thiazocin-4-yl, 1,2,3,4,5,6-hexahydro-1-benzazocin-1-yl, 1,2,3,4,5,6-hexahydro-2-benzazocin-2-yl, 1,2,3,4,5,6-hexahydro-3-benzazocin-3-yl, 1,2,3,4,5,6-hexahydroazocin-1-yl, 1,2,3,4,7,8-hexahydroazocin-1-yl and 1,2,3,4,5,8-hexahydroazocin-1-yl; Those formed by methylene group, taken together with the adjacent nitrogen atom, in which one or two methylene groups may optionally be substituted with one or two oxygen atoms and/or sulfur atoms, e.g. 3-oxazolidinyl, 4-morpholinyl, 3-thiazolidinyl and 4-thiomorpoholinyl.

The said N-containing saturated heterocyclic group may optionally be substituted, and its substituent is exemplified by (1) a $C_{1-6}$ alkyl group, e.g. methyl, ethyl and n-propyl, (2) phenyl, (3) halogen, e.g. fluorine, chlorine, bromine and iodine, (4) nitro, (5) cyano, (6) hydroxy, (7) oxo, (8) a $C_{1-6}$ alkoxy group, e.g. methoxy, ethoxy and n-propoxy, (9) amino and (10) a mono- or di- $C_{1-6}$ alkylamino group, e.g. methylamino, ethylamino, propylamino, dimethylamino and diethylamino.

Preferable examples of the said N-containing saturated heterocyclic group include those formed by methylene group, taken together with the adjacent nitrogen atom, e.g. pyrrolidinyl, piperidyl, heptamethyleneimino, imidazolidinyl, piperazinyl, pyrazolidinyl, hexamethyleneimino, 1,2-dihydropyridin-1-yl, and 1,2,3,6-tetrahydropyridin-1-yl, and those formed by methylene group, taken together with the adjacent nitrogen atom in which one or two methylene groups may optionally be substituted with one or two oxygen atoms and/or sulfur atoms, e.g. oxazolidinyl, morpholinyl, thiazolidinyl and thiomorpholinyl.

Among them as the N-containing saturated heterocyclic group which is formed by combination of $R^2$ and $R^3$ taken together with the adjacent nitrogen atom, hexamethylenimino and piperidiyl which is substituted with a $C_{1-6}$ alkyl group are especially preferable.

The N-containing saturated heterocyclic group may optionally form a condensed ring with a benzene ring on the two carbon atoms adjacent to each other in the said heterocyclic ring, and the examples include benzothiazolidine, tetrahydroquinoline, tetrahydroisoquinoline, indoline and isoindoline.

Preferable example of the peptide of this invention further include a compound represented by the formula, X—B—CH($R^4$)—C(=O)—$X^1$—CH($R^5$)—C(=$X^2$)—NH—CH($R^6$)—(CH$_2$)n—C(=O)—Y, or a salt thereof, wherein X is a group represented by the formula $R^1$—CO—, wherein $R^1$ is of the same meaning as defined above or a group represented by the formula $R^2R^3$N—CO—, wherein $R^2$ or $R^3$ is of the same meaning as defined above, B is an oxgen atom or a group of the formula —$NR^7$—, wherein $R^7$ is a hydrogen atom or a hydrocarbon residue, $R^4$ is a hydrocarbon residue or a heterocyclic group, $X^1$ is an oxgen atom or a group of the formula —$NR^8$—, wherein $R^8$ is a hydrogen atom or a hydrocarbon residue, $R^5$ is an optionally substituted heterocyclic-alkyl group, $X^2$ is an oxgen atom or a sulfur atom, $R^6$ is an optionally substituted hydrocarbon residue, n is an integer of 0 or 1, Y is an amino acid residue which is substituted with a carboxyl group or a heterocyclic group capable of releasing proton and wherein one carboxyl group is amidated with an optionally substituted N-containing heterocyclic group. In the above formula, examples of a hydrocarbon residue of $R^4$, a hydrocarbon residue of the optionally substituted hydrocarbon residue of $R^6$, a hydrocarbon residue $R^7$ and a hydrocarbon residue of $R^8$ include the same ones as defined above. As the substituent of the optionally substituted hydrocarbon residue of $R^6$, include the same ones as those of the hydrocarbon residue defined above.

Examples of the heterocyclic groups of $R^4$ include the same ones as those of the heterocyclic group defined above.

Examples of the heterocyclic group in the optionally substituted heterocyclic-alkyl group of $R^5$ include the same ones as those of the heterocyclic group defined above. Examples of the alkyl group in the optionally substituted heterocyclic-alkyl group of $R^5$ include the same ones of the above-mentioned alkyl group. Examples of the substituent of the heterocyclic group of $R^5$ include the same ones of the above-mentioned heterocyclic group.

Further preferable peptide of this invention include those represented by the formula, X—$A_{11}$—$A_{12}$—$A_{13}$—Y wherein X is an acyl group, $A_{11}$, $A_{12}$ and $A_{13}$ are optionally substituted amino acid residues, Y is an amino acid residue which is substituted with a carboxyl group or a heterocyclic group capable of releasing proton and wherein one carboxyl group is amidated with an optionally substituted heterocyclic group.

The amino acid residue of $A_{11}$, $A_{12}$ or $A_{13}$ are naturally-occurring or non-naturally-occurring amino acid residue, which may be of either D- or L-configuration.

Examples of the said naturally-occurring amino acid include glycine, alanine (α-alanine, β-alanine), valine, leucine, isoleucine, serine, threonine, cysteine, cystine, methionine, aspartic acid, glutamic acid, lysine, arginine, phenylalanine, tyrosine, histidine, tryptophane, proline and oxyproline. Among them, α-amino acid and β-alanine are preferable.

Examples of the non-naturally-occurring amino acid include norleucine, γ-methylleucine, tert-leucine, norvaline, homoarginine, homoserine, aminoisobutyric acid and ornithine.

Examples of the substituent on said amino acid include (1) a $C_{1-6}$ alkyl group, e.g. methyl, ethyl, n-propyl, isopropyl, n-propyl, isopropyl, sec-butyl, tert-butyl and n-pentyl, and preferably a $C_{1-3}$ alkyl group, (2) cyano, (3) halogen, e.g. fluorine, chlorine, bromine and iodine, (4) a hydroxy-$C_{1-6}$ alkyl group, e.g. hydroxymethyl and hydroxyethyl. In the case where amino acid is tryptophane, in addition to these groups, (5) a $C_{1-6}$ alkoxy group, e.g. methoxy, ethoxy, n-propoxy, isopropoxy, n-butoxy and tert-butoxy, and preferably a $C_{1-3}$ alkoxy group, (6) a $C_{1-6}$ alkoxy-carbonyl group, e.g. methoxycarbonyl, ethoxycarbonyl, isopropoxycarbonyl and tert-butoxycarbonyl, and preferably a $C_{1-3}$ alkoxy-carbonyl group, (7) a $C_{1-4}$ acyl group, e.g. formyl, acetyl, propionyl and butyryl, (8) hydroxy and (9) a group of the formula: —S(O)$_a$—R$^{21}$, wherein a is an integer of 0 to 2 and R$^{21}$ is a $C_{1-6}$ alkyl group, specific examples are the same as described above, e.g. methylthio, methanesulfinyl, methanesulfonyl, ethylthio, ethanesulfinyl and ethanesulfonyl.

The amino acid residue of Y which is substituted with a carboxyl group or a heterocyclic group capable of releasing proton and one carboxyl group is amidated with an optionally substituted heterocyclic group, has the same meaning as defined above.

Further examples of a preferable peptide of this invention include peptide derivative represented by the formula R$^{1'}$—CO—A$_1$—A$_2$—A$_3$—A$_4$, wherein R$^{1'}$ is an optionally substituted N-containing saturated heterocyclic group which is combined on a nitrogen atom, A$_1$ is Leu, Ile or Nle, A$_2$ is an optionally substituted D-Trp, A$_3$ is D-Leu, D-Ile or D-Nle, and A$_4$ is Asp, Glu, tetrazolyl-α-Ala or tetrazolyl-β-Ala wherein one carboxyl group of A$_4$ is amidated with an optionally substituted heterocyclic group.

A$_1$ is especially preferable Leu.

Examples of the substituent of the optionally substituted D-Trp of A$_2$ include (1) a $C_{1-6}$ alkyl group, e.g. methyl, ethyl, n-propyl, isopropyl, n-butyl, isobutyl, sec-butyl, tert-butyl and n-pentyl, and preferably is a $C_{1-3}$ alkyl group, (2) a $C_{1-6}$ alkoxy group, e.g. methoxy, ethoxy, n-propoxy, isopropoxy, n-butoxy and tert-butoxy, and preferably is a $C_{1-3}$ alkoxy group, (3) a $C_{1-6}$ alkoxy-carbonyl group, e.g. methoxycarbonyl, ethoxycarbonyl, isopropoxycarbonyl and tert-butoxycarbonyl, and preferably is a $C_{1-3}$ alkoxy-carbonyl group, (4) a $C_{1-6}$ acyl group, e.g. formyl, acetyl, propionyl and butyryl, (5) cyano, (6) halogen, e.g. fluorine, chlorine, bromine and iodine, (7) hydroxy, (8) a hydroxy-$C_{1-6}$ alkyl group, e.g. hydroxymethyl and hydroxyethyl and (9) a group of the formula: —S(O)—R$^{21}$, wherein a is an integer of 0 to 2, R$^{21}$ is a $C_{1-6}$ alkyl group, specific examples are the same as described above, e.g. methylthio, methanesulfinyl, methanesulfonyl, ethylthio, ethanesulfinyl and ethanesulfonyl. Among them, a $C_{1-6}$ alkoxycarbonyl group and a $C_{1-6}$ acyl group are preferable, and, methoxycarbonyl and formyl are especially preferable. The number of these substituent is 1 to 3, preferably 1 to 2. Especially preferable A$_2$ is D-Trp substituted with a $C_{1-6}$ alkoxy-carbonyl group.

Especially preferable A$_3$ is D-Nle.

The optionally substituted heterocyclic group of A$_4$ include the same ones as described above, preferably exemplified by an optionally substituted 5- to 8-membered heterocyclic group containing 1 to 3 nitrogen atoms. Among them, an optionally substituted piperazinyl group is preferable.

Examples of the preferable substituent of the heterocyclic group for A$_4$ include an optionally substituted $C_{6-14}$ aryl group defined as above-mentioned.

As the A$_4$, Asp or Glu, which is amidated with a 5- to 8-membered heterocyclic group containing 1 to 3 nitrogen atoms, and which is substituted with a $C_{6-14}$ aryl group which may optionally have a halogen group, a $C_{1-6}$ alkyl group (defined as above) or a $C_{1-6}$ alkoxy group (defined as above) is preferable.

The peptide of the present invention include a salt thereof. Such salt includes a salt with a base when the peptide is acidic, and a salt with an acid when the peptide is basic. Example of the salt of the peptide with a base include a pharmaceutically acceptable salt such as an alkaline metal salt, e.g. sodium salt and potassium salt, an alkaline earth metal salt, e.g. calcium salt and magnesium salt, an ammonium salt and an organic base salt, e.g. pyridine salt and triethylamine salt. Example of the salt of the peptide with an acid include a pharmaceutically acceptable salt such as an inorganic acid salt, e.g. hydrochloride, sulfate and nitrate, and an organic acid salt, e.g. acetate, oxalate and p-toluenesulfonate.

The peptide derivative or a salt thereof of the present invention can be produced by a per se known conventional means of peptide production or a method based thereon, whether it is based on solid-phase synthesis or liquid-phase synthesis, for instance. Accordingly, the desired peptide can be produced by condensing the partial peptide or amino acids capable of constituting the peptide and the remaining moiety, and, when the product has a protected group, deprotecting the product. Example methods of condensation or deprotection include the following methods (1) to (5):

(1) M. Bodanszky and M. A. Ondetti, Peptide Synthesis, Interscience Publishers, New York (1966)

(2) Schroeder and Luebke, The Peptide, Academic Press, New York (1965)

(3) Nobuo Izumiya et al., Foundation of Peptide Synthesis and Experiment (Peptide Gosei no Kiso to Jikken), Maruzen (1975)

(4) Haruaki Yajima and Shunpei Sakakibara, Lecture of Biochemical Experiment 1 (Seikagaku Jikken Koza 1), Chemistry of Protein IV (Tanpakushitsu no Kagaku IV), 205 (1977)

(5) Compiled under the supervision of Haruaki Yajima, Development of Pharmaceuticals, second series (Zoku Iyakuhin no Kaihatsu), Vol. 14, Peptide Synthesis, Hirokawa Shoten For the production of the peptide derivative or a salt thereof of the present invention, the following methods are mentioned;

(a) A peptide derivative, whose C-terminal is the amino acid residue which is amidated with an optionally substituted heterocyclic group, and substituted with a carboxyl group, can be produced by subjecting a peptide derivative whose C-terminal is the amino acid residue which is amidated with an optionally substituted heterocyclic group, and substituted with a protected carboxyl group to the elimination reaction of the protective group, i.e. a deprotection reaction, and (b) a peptide derivative, whose C-terminal is the amino acid residue which is amidated with an optionally substituted heterocyclic group, and substituted with a heterocyclic group capable of releasing proton, and N-terminal is acylated by the acyl group, can be produced by subjecting a peptide whose C-terminal is the amino acid residue which is amidated with an optionally substituted heterocyclic group, and substituted with a heterocyclic group capable of releasing proton, and a peptide whose N-terminal is acylated by the acyl group, to a condensation reaction.

The condensation reaction is conducted by dissolving the starting compound, depending on necessity after removing the protecting group, in an adequate solvent, e.g. DMF, to which is added an adequate condensing agent, e.g. water-soluble carbodiimide, e.g. WSCD; an additive, e.g. HONB, then by allowing the reaction to proceed at room temperatures, about 0 to 30° C., for about 8 to 16 hours.

When the protective group for amino is tert-butyl, the deprotection reaction is conducted by dissolving the relevant compound in a solvent, e.g. ether, dioxane, tetrahydrofuran or ethyl acetate, adding thereto a reagent, e.g. hydrogen chloride gas or solution prepared by introducing hydrogen chloride gas into the above-mentioned solvent, and allowing the reaction to proceed at about −5° C. to 25° C. for about 0.5 to 2 hours. Or, the deprotection reaction can be conducted by dissolving the relevant compound in trifluoroacetic acid and allowing the reaction to proceed at −5° C. to 25° C. for 5 minutes to 30 minutes.

When the protective group for carboxyl is Bzl, the deprotection is conducted by dissolving the relevant compound in a solvent, e.g. dioxane, tetrahydrofuran, methanol, ethanol or dimethylformamide and allowing the reaction to proceed while introducing hydrogen gas at about 0 to 30° C. for 1 to 5 hours using palladium black as the catalyst.

When the protective group for carboxyl is Pac, the deprotection is conducted by dissolving the relevant compound in a solvent (e.g. aqueous solution of acetic acid), adding thereto powdery metallic zinc, and allowing the reaction to proceed at about 0 to 30° C. for 0.5 to 0.5 to 3 hours.

When the protective group for carboxyl is 9-fluorenylmethyl, the deprotection is conducted by dissolving the relevant compound in a solvent (e.g. DMF, pyridine, tetrahydrofuran or dioxane), adding thereto a reagent (e.g. piperidine, triethylamine or tetrabutyl ammonium fluoride), and allowing the reaction to proceed at about −5 to 30° C. for 0.5 to 3 hours.

After completion of the reaction, conventional purification methods such as solvent-extraction, distillation, column chromatography, liquid chromatography and recrystallization can be employed in combination to purify and isolate the peptide.

An exemplary method of introducing the above-mentioned groups is as follows: the amino group of Asp or Glu is introduced, by a conventional means or a means based thereon, into the remainder carboxyl group of the compound in which carboxyl groups at the α- or ω- position (β-position, γ-position) are protected with groups adequate to protect the carboxyl group in the reaction conditions, followed by condensation of D-Nle by a conventional means in the field of peptide synthesis; then, an optionally substituted D-Trp obtainable by a conventional means in the field of indole chemistry is condensed; this condensate is further condensed with $R^1CO-A_1$ moiety obtainable by combination of $R^1CO$-halide, e.g. chloride and $A_1$ or combination of $R^1$, $A_1$ and carbonyldiimidazole and then, the protective group is removed, or, the carboxyl group at the α- or ω-position of Asp or Glu is protected by a means which is capable of removing the protective group selectively, then, D-Nle, $A_2$ and $R^1-CO-A_1$ are condensed by a conventional means; then only one of the carboxyl groups at the α- or ω-position is removed, to which the object substituent is introduced, then the remaining protective groups are removed to obtain the desired peptide.

The peptide derivative or a salt thereof of the present invention exhibits endothelin receptor-antagonistic action. The endothelin may, for example, be any of the endothelin-1, -2 and -3 as described in Pharmacia, Vol. 26, pp.21–24 (1990); the antagonist of the present invention exhibits antagonistic action on both of known two types ($ET_A$, $ET_B$) of endothelin receptors [cf: $ET_A$, $ET_B$: Trends in Pharmaceutical Science (1995) RECEPTOR & ION CHANNEL NOMENCLATURE SUPPLEMENT p.28].

The peptide derivative or a salt thereof exhibits remarkable endothelin antagonistic action, which is low in toxicity, and can be used for the therapy or prophylaxis of, for example, asthma, cerebral apoplexy, angina pectoris, acute renal failure, myocardial infarction, cerebral vasospasm, cerebral infarction, arteriosclerosis, multiple organ failure caused by endotoxin, renal damage induced by cyclosporin, pulmonary hypertension and Raynaud's disease.

When the peptide derivative or a salt thereof are used for a prophylactic or therapeutic agent of the above-mentioned diseases, the peptide derivative or a salt thereof can be orally or non-orally administered in the form of a liquid or solid to humans or mammals, e.g. rabbits, dogs, cats, rats or mice. It is a common practice to non-orally administer in the form of a liquid preparation, e.g. injection.

Although the dosage varies with e.g. subject patients, subject diseases, symptoms and administration method, for non-oral use in treating adult of above-mentioned diseases it is advantageous to administer the peptide derivative or a salt thereof in the form of an injection at about 0.01 to 50 mg, preferably about 0.05 to 20 mg, per kg body weight, about 1 to 3 times daily by intravenous injection. For oral administration, one dose in terms of the weight of the peptide derivative ranges usually from about 5 mg to 1 g, preferably about 10 to 100 mg per kg body weight, 1 to 3 times daily.

Injections include, besides intravenous injections, subcutaneous, intracutaneous, intramuscular and drip infusion injections. These injections are prepared by a per se known method, i.e. dissolving, suspending or emulsifying the peptide in a sterile aqueous or oily solution.

Examples of the aqueous solution for injection include distilled water for injection, physiological saline and isotonic solutions containing glucose or other auxiliaries, e.g. D-sorbitol, D-mannitol and sodium chloride, which may optionally be used in combination with an adequate solubilizer such as alcohol, e.g. ethanol; polyalcohol, e.g. propylene glycol; and polyethylene glycol and a nonionic surfactant, e.g. Polysorbate 80 (registered trademark) and HCO-50 (registered trademark). Examples of the oily solution include sesame oil and soybean oil, which may optionally be used in combination with a solubilizer such as benzyl benzoate and benzyl alcohol. In addition, a buffering agent, e.g. phosphate buffer and sodium acetate buffer, a local anesthetic, e.g. benzalkonium chloride and procaine hydrochloride, a stabilizer, e.g. human serum albumin and polyethylene glycol, and a preservative, e.g. benzyl alcohol and phenol may optionally be incorporated. The injectable solution thus prepared is usually packaged in an appropriate ampule.

For the oral administration, powdery preparations, tablets, granules and capsules, for example, are used. For formulation of such oral administrable preparations as above, pharmaceutically acceptable carriers can be incorporated. Examples of such carriers include excipients, e.g. lactose and starch; lubricants, e.g. magnesium stearate and talc; binding agents, e.g. hydroxypropyl cellulose, hydroxypropylmethyl cellulose and macrogol; and disintegrants, e.g. starch and carboxymethyl cellulose calcium. And, depending on necessity, such additives as preservatives, e.g. benzyl alcohol, chlorobutanol, methyl para-hydroxybenzoate and propyl para-hydroxybenzoate; antioxidants; coloring agent; and sweeteners can be optionally employed.

In the present specification, unless otherwise specified, amino acid is of L-configuration.

In the present specification, the following abbreviations in common use in relevant fields are used in some instances.
Leu: Leucine
Ile: Isoleucine
Nle: Norleucine
Asp: Aspartic acid
Glu: Glutamic acid
Ala: Alanine
Abu: Aminobutyric acid
Trp(CHO): $N^{in}$-formyltryptophan
Trp(COOMe): $N^{in}$-carboxymethyltryptophan
Php: 1-phenylpiperazine
2MeOPhp: 1-(2-methoxyphenyl)piperazine
3MeOPhp: 1-(3-methoxyphenyl)piperazine
2MeO-5MePhp: 1-(2-methoxyl-5-methylphenyl)piperazine
2FPhp: 1-(2-fluorophenyl)piperazine
Boc :tert-butoxycarbonyl
HOBt: N-hydroxybentriazole
HONB: N-hydroxy-5-norbornene-2,3-dicarboxyimide
ONB: 5-norbornene-2,3-dicarboxyimide ester
Bzl: benzyl
Pac: Phenacyl
p-Tos: p-toluenesulfonyl
WSCD: 1-ethyl-3-(3-dimethylaminopropyl)carbodiimide
CDI: Carbonyl diimidazole
TEA: Triethylamine
DCHA: Dicyclohexylamine
DMF: N,N-dimethylformamide
DCM: Dichloromethane
THF: Tetrahydrofuran
Fmoc: 9-fluorenylmethyloxycarbonyl
Z: Benzyloxycarbonyl (carbobenzoxy)
Acp: (R)-3-amino-3-cyanopropionic acid
Atp: (R)-3-amino-3-[(1H)-tetrazol-5-yl]propionic acid
COOMe: methoxycarbonyl Industrial Application Since peptide derivatives or a salt thereof of the present invention exhibit remarkable endothelin receptor-antagonistic action with low toxicity, they can be used advantageously as medicines for prophylaxis and therapy of, for example, cardio or cerebro circulatory diseases, hepatic diseases and/or renal diseases.

By the following working examples and test examples, the present invention will be illustrated more concretely, and they should not be construed as limiting this invention.

For determination of melting points in the following working examples, a device for determination of melting points manufactured by Yanagimoto Seisakusho was employed. % indicates weight %, unless otherwise specified. Eluents employed for TLC Rf1: $CHCl_3/CH_3OH=95/5$,
Rf2: $CHCl_3/CH_2OH/CH_3COOH=90/10/5$ (each ratio is indicated as volume ratio)

The conditions of eluting samples by HPLC (High Performance Liquid Chromatography) are as follows Column: R-ODS-5-ST (4.6 mm×15 cm, mfd. by YMC, Inc.)
Mobile phase: Solution A: $H_2O$ (0.1% TFA)
Solution B: $CH_3CN$ (0.1% TFA)
Gradient: 0% B one minute
then from 0% B to 70% B (2%/min.)
Flow rate: 1 ml/min.

WORKING EXAMPLE 1

Production of Hexamethyleniminocarbonyl-Leu-D-Trp(CHO)-D-Nle-D-Asp(Php)

(I) Production of Boc-D-Asp(Php)-OBzl

A solution of 672 μl of 1-phenylpiperazine in 10 ml of DMF was ice-cooled, to which was added an acetonitrile solution of Boc-D-Asp(ONB)-OBzl prepared from 1.29 g of Boc-D-Asp-OBzl, 788 mg of HONB and 841 mg of WSCD.HCl. The mixture was stirred overnight at room temperature. The reaction mixture was concentrated, which was dissolved in ethyl acetate. This solution was washed with 1N HCl and a 4% aqueous solution of $NaHCO_3$, which was further washed with water, followed by drying over $Na_2SO_4$. The resultant was concentrated, to which was added ether to give precipitates. The precipitates were collected by filtration. The yield: 1.83 g (98%), m.p. 70–71° C., Rf1: 0.73 Rf2: 0.83, MS: (M+H+)=468 (theoretical value)=468

(II) Production of Boc-D-Nle-D-Asp(Php)-OBzl

In 10 ml of 4N—HCl/ethyl acetate was dissolved 701 mg of Boc-D-Asp(Php)-OBzl produced in Working Example 1 (I). The solution was stirred for 30 minutes under ice-cooling, followed by concentration. To the concentrate was added ether to give precipitates. The precipitates were collected by filtration and dried, which was dissolved in 15 ml of DMF. The solution was ice-cooled, to which was added 210 μl of TEA. To the mixture was added Boc-D-Nle-ONB prepared from 681 mg of Boc-D-Nle.DCHA, 323 mg of HONB and 1344 mg of WSCD.HCl, which was stirred overnight at room temperature. The reaction mixture was concentrated, which was dissolved in ethyl acetate. The solution was washed with 1N HCl and a 4% aqueous solution of $NaHCO_3$, which was further washed with water, followed by drying over $Na_2SO_4$ and concentration. The yield: 674 mg (77%), Rf1: 0.62 Rf2: 0.72, MS: (M+H+)= 581 (theoretical value)=581

(III) Production of Boc-D-Trp(CHO)-D-Nle-D-Asp(Php)-OBzl

In 10 ml of 4N—HCl/ethyl acetate was dissolved 116 mg of Boc-D-Nle-D-Asp(Php)-OBzl produced in Working Example 1 (II). The solution was stirred for 30 minutes under ice-cooling, which was concentrated. To the concentrate was added ether to give precipitates. The precipitates were collected by filtration and dried, which was dissolved in 15 ml of DMF. The solution was ice-cooled, to which was added 42 μl of TEA. To the mixture was added Boc-D-Trp (CHO)-ONB prepared from 73 mg of Boc-D-Trp(CHO), 43 mg of HONB and 146 mg of WSCD.HCl, which was stirred overnight at room temperature. The reaction mixture was concentrated, which was dissolved in ethyl acetate. The solution was washed with 1N HCl and a 4% aqueous solution of $NaHCO_3$, which was further washed with water, followed by drying over $Na_2SO_4$ and concentration. To the concentrate was added ether to give precipitates, which were collected by filtration. Yield: 143 mg (90%), m.p.120–122° C., Rf1: 0.45 Rf2: 0.59, MS: (M+H+)=795 (theoretical value)=795

(IV) Production of hexamethyleniminocarbonyl-Leu-D-Trp (CHO)-D-Nle-D-Asp(Php)-OBzl In 5 ml of 4N—HCl/ethyl acetate was dissolved 79 mg of Boc-D-Trp(CHO)-D-Nle-D-Asp(Php)-OBzl produced in Working Example 1 (III). The solution was stirred for 30 minutes under ice-cooling, which was then concentrated. To the concentrate was added ether to give precipitates. The precipitates were collected by filtration and dissolved in 5 ml of DMF. The solution was ice-cooled, to which were added 26 mg of hexamethyleniminocarbonyl-Leu, 54 mg of HOBt, 38 mg of WSCD.HCl and 21 μl of TEA, successively. The mixture was stirred overnight at room temperature. The reaction mixture was concentrated, which was dissolved in ethyl acetate. The solution was washed with 1N HCl and a 4% aqueous solution of NaHCO$_3$, which was further washed with water, followed by drying over Na$_2$SO$_4$ and concentration. To the concentrate was added ether to give precipitates, which were collected by filtration. Yield: 92 mg (98%), m.p.111–113° C. Rf1: 0.38 Rf2: 0.53, MS: (M+H+)= 993 (theoretical value)=993

(V) Production of hexamethyleniminocarbonyl-Leu-D-Trp(CHO)-D-Nle-D-Asp(Php)

In 10 ml of DMF was dissolved 47 mg of hexamethyleniminocarbonyl-Leu-D-Trp(CHO)-D-Nle-D-Asp(Php)-OBzl produced in Working Example 1 (IV). The solution was subjected to catalytic reduction for 3 hours in hydrogen streams using Pd black as the catalyst. The catalyst was filtered off, and the residue was dissolved in a small volume of acetic acid. To the solution was added water, which was freeze-dried. The freeze-dried product was purified by means of HPLC using a column manufactured by YMC Inc. D-ODS-5-ST(2 cm×15 cm) to afford hexamethyleniminocarbonyl-Leu-D-Trp(CHO)-D-Nle-D-Asp(Php). Yield: 5.2 mg (25%), MS: (M+H+)=843 (theoretical value)=843, Eluting time: 32.2 minutes

WORKING EXAMPLE 2

Production of Hexamethyleniminocarbonyl-Leu-D-Trp(COOMe)-D-Nle-D-Asp(Php)

(I) Production of Boc-D-Trp-OBzl

To a solution of 45.7 g of Boc-D-Trp in a mixture of 200 ml of CH$_3$OH and 20 ml of water. To the solution was added 25.7 g of Cs$_2$CO$_3$, which was concentrated under reduced pressure. The concentrate was then dissolved in 50 ml of DMF, which was concentrated under reduced pressure. This procedure was repeated twice, and the resulting concentrate was dissolved in 100 ml of DMF. To the solution was added, under ice-cooling, 19.6 ml of benzyl bromide. The mixture was stirred overnight at room temperature. The reaction mixture was concentrated, which was dissolved in ethyl acetate. The solution was sequentially washed with 1N HCl and a 4% aqueous solution of NaHCO$_3$, which was further washed with water, followed by drying over Na$_2$SO$_4$ and concentration. The concentrate was recrystallized from a mixture of ethyl acetate and ether to afford the object product. Yield: 53.9 g (91%), m.p.143–144° C., Rf1: 0.53 Rf2: 0.74

(II) Production of Boc-D-Trp(COOMe)-OBzl

In 25 ml of DCM was dissolved 1.97 g of Boc-D-Trp-OBzl produced in Working Example 2 (I). The solution was ice-cooled, to which were added sequentially 17 mg of tetrabutyl ammonium hydrogensulfate, 580 μl of methyl chlorocarbonate and 500 mg of sodium hydroxide. The mixture was stirred for 2 hours at room temperature, to which was then added 0.5N—HCl to render the pH to 2. The mixture was separated into two layers, and the DCM layer was washed with water, followed by drying over Na$_2$SO$_4$ and concentration. To the concentrate was added ether, then resulting precipitates were collected by filtration. Yield: 2.07 g (92%), m.p.111–113° C., Rf1: 0.79 Rf2: 0.89

(III) Production of Boc-D-Trp(COOMe)—OH

In 40 ml of CH$_3$OH was dissolved 0.68 g of Boc-D-Trp(COOMe)-OBzl produced in Working Example 2 (II). The solution was subjected to catalytic reduction for 5 hours in hydrogen streams using Pd black as the catalyst. The catalyst was filtered off, and the filtrate was concentrated. To the concentrate was added ether-petroleum ether to give precipitates, which were collected by filtration. Yield: 0.47 g (87%), m.p.83–85° C., Rf1: 0.15 Rf2: 0.49

(IV) Production of hexamethyleniminocarbonyl-Leu-D-Trp(COOMe)-D-Nle-D-Asp(Php)

In 10 ml of DMF was dissolved, 148 mg of hexamethyleniminocarbonyl-Leu-D-Trp(COOMe)-D-Nle-D-Asp Php-OBzl produced substantially the same manner as in Working Example 1 using Boc-D-Trp(COOMe)—OH produced in Working Example 2 (III). The solution was subjected to catalytic reduction for 3 hours in hydrogen streams using Pd black as the catalyst. The catalyst was filtered off, and the filtrate was dissolved in a small volume of acetic acid. To the solution was added water, which was freeze-dried. The freeze-dried product was purified by means of HPLC using a column manufactured by YMC Inc. D-ODS-5-ST (2 cm×15 cm) to afford hexamethyleniminocarbonyl-Leu-D-Trp(COOMe)-D-Nle-D-Asp(Php). Yield: 4.5 mg (21%), MS: (M+H+)=873 (theoretical value)=873, Eluting time: 34.0 minutes

WORKING EXAMPLE 3

Production of Hexamethyleniminocarbonyl-Leu-D-Trp(COOMe)-D-Nle-Asp (Php)

(I) Production of Boc-Asp(Php)-OBzl

In 10 ml of DMF was dissolved 153 μl of 4-phenylpiperazine. The solution was ice-cooled, to which was added an acetonitrile solution of Boc-Asp(ONB)-OBzl prepared from 323 mg of Boc-Asp-OBzl, 197 mg of HONB and 200 mg of WSCD.HCl. The mixture was stirred overnight at room temperature. The reaction mixture was concentrated, which was dissolved in ethyl acetate. The solution was sequentially washed with 1N HCl and a 4% aqueous solution of NaHCO$_3$, which was further washed with water, followed by drying over Na$_2$SO$_4$ and concentration. To the concentrate was added a mixture of ether and petroleum ether to give precipitates, which were collected by filtration. Yield: 397 mg (85%), m.p.68–69° C. Rf1: 0.71 Rf2: 0.81

(II) Production of hexamethyleniminocarbonyl-Leu-D-Trp(COOMe)-D-Nle-Asp(Php)

In 10 ml of DMF was dissolved 148 mg of hexamethyleniminocarbonyl-Leu-D-Trp(COOMe)-D-Nle-Asp(Php)-OBzl produced in substantially the same manner as in Working Example 2 using Boc-Asp(Php)-OBzl produced in Working Example 3 (I). The solution was subjected to catalytic reduction for 3 hours in hydrogen streams using Pd black as the catalyst. From the reaction mixture, the catalyst was filtered off. The filtrate was dissolved in a small volume of acetic acid, to which was added water, followed by freeze-drying. The freeze-dried product was purified by means of HPLC using a column manufactured by YMC Inc. D-ODS-5-ST (2 cm×15 cm) to give hexamethyleneiminocarbonyl-Leu-D-Trp(COOMe)-D-Nle-Asp(Php). Yield: 5.3 mg (24%), MS: (M+H+)=873 (theoretical value)=873, eluting time: 34.0 minutes

WORKING EXAMPLE 4

Production of Hexamethyleniminocarbonyl-Leu-D-Trp(COOMe)-D-Nle-D-Glu-Php (I) Production of Boc-D-Glu(OBzl)-Php A solution of 153 μl in 10 ml of DMF was ice-cooled, to which was added an acetonitrile solution of Boc-D-Glu(OBzl)-ONB prepared from 337 mg of Boc-D-Glu(OBzl), 197 mg of HONB and 200 mg of WSCD.HCl. The mixture was stirred overnight at room temperature. The reaction mixture was concentrated, which was dissolved in ethyl acetate. This solution was washed with 1N HCl and a 4% aqueous solution of NaHCO3, which was further washed with water, followed by drying and concentration. To the concentrate was added ether to give precipitates, which were collected by filtration. Yield: 430 mg (89%), Rf1: 0.79 Rf2: 0.83

(II) Production of hexamethyleniminocarbonyl-Leu-D-Trp (COOMe)-D-Nle-D-Glu-Php

In 10 ml of DMF was dissolved 49 mg of hexamethyleniminocarbonyl-Leu-D-Trp(COOMe)-D-Nle-D-Glu(OBzl)-Php produced by substantially the same procedure as in Working Example 2, using Boc-D-Glu(OBzl)-Php produced in Working Example 4 (I). The solution was subjected to catalytic reduction for 3 hours in hydrogen steams in the presence of Pd black as the catalyst. The catalyst was filtered off. The filtrate was dissolved in a small volume of acetic acid. To the solution was added water, which was freeze-dried. The freeze-dried product was purified by means of HPLC using a column manufactured by YMC Inc. D-ODS-5-ST(2 cm×15 cm). Yield: 6.2 mg (28%), MS:(M+H+)=887 (theoretical value)=887, eluting time: 34.3 minutes

WORKING EXAMPLE 5

Production of Hexamethyleniminocarbonyl-Leu-D-Trp(COOMe)-D-Nle-D-Asp (2MeOPhp)

(I) Production of Boc-D-Asp (OPac)-OBzl

To a solution of 13.23 g of Boc-D-Asp-OBzl in a mixture of 20 ml of $CH_3OH$ and 2 ml of water was added 1.72 g of $Cs_2CO_3$. The mixture was concentrated under reduced pressure. The concentrate was dissolved in 20 ml of toluene, which was concentrated under reduced pressure. This procedure was repeated twice. The resulting concentrate was dissolved in 20 ml of DMF, to which was added under ice-cooling 2.18 g of 2-bromoacetophenone. The mixture was stirred for 3 hours at room temperature. The reaction mixture was concentrated, which was dissolved in ethyl acetate. The solution was washed with 1N HCl and a 4% aqueous solution of $NaHCO_3$, which was further washed with water, followed by drying over $Na_2SO_4$ and concentration. To the concentrate was added ether to give precipitates, which were collected by filtration. Yield: 3.78 g (86%), m.p.72–74° C., Rf1: 0.82 Rf2: 0.89

(II) Production of hexamethyleniminocarbonyl-Leu-D-Trp (COOMe)-D-Nle-D-Asp-OBzl

In 20 ml of a 90% aqueous solution of $CH_3COOH$ was dissolved 1.87 g of hexamethyleniminocarbonyl-Leu-D-Trp (COOMe)-D-Nle-D-Asp(OPac)-OBzl produced by substantially the same procedure as in Working Example 2, using Boc-D-Asp(OPac)-OBzl produced in Working Example 5 (I). To the solution was added, under ice-cooling, 6.54 g of Zn. The mixture was stirred for 3 hours at room temperature. From the reaction mixture, Zn was filtered off, and the filtrate was concentrated, which was dissolved in ethyl acetate. The solution was washed with 1N HCl, which was washed with water, followed by drying over $Na_2SO_4$ and concentration. To the concentrate was added ether-petroleum ether to precipitate out the titled compound, which was collected by filtration. Yield: 960 mg (59%), Rf1: 0.27 Rf2: 0.53

(III) Production of hexamethyleniminocarbonyl-Leu-D-Trp (COOMe)-D-Nle-D-Asp(2MeOPhp)-OBzl In 10 mg of DMF was dissolved 23 mg of 1-(2-methoxyphenyl)piperazine hydrochloride. To the solution were added 166 mg of hexamethyleniminocarbonyl-Leu-D-Trp(COOMe)-D-Nle-D-Asp-OBzl produced in Working Example 5 (II), 43 mg of HOBt, 31 mg of WSCD.HCl and 22 µl of TEA. The mixture was stirred overnight at room temperature. The reaction mixture was concentrated, which was dissolved in ethyl acetate. The solution was washed with 1N HCl and a 4% aqueous solution of $NaHCO_3$, which was further washed with water, followed by drying over $Na_2SO_4$ and concentration. To the concentrate was added ether to precipitate out the title compound, which was collected by filtration. Yield: 69 mg (69%), Rf1: 0.46 Rf2: 0.62

(IV) Production of hexamethyleniminocarbonyl-Leu-D-Trp (COOMe)-D-Nle-D-Asp (2MeOPhp)

In 10 ml of DMF was dissolved 50 mg of hexamethyleniminocarbonyl-Leu-D-Trp(COOMe)-D-Nle-D-Asp(2MeOPhp)-OBzl. The solution was subjected to catalytic reduction for 3 hours in hydrogen streams using Pd black as the catalyst. The catalyst was filtered off, and the filtrate was dissolved in a small volume of acetic acid. To the solution was added water, which was freeze-dried, followed by purification by means of HPLC using a column D-ODS-5-ST(2 cm×15 cm) manufactured by YMC Inc. to afford hexamethyleniminocarbonyl-Leu-D-Trp(COOMe)-D-Nle-D-Asp (2MeOPhp). Yield: 5.1 mg (23%), MS: (M+H+)=903 (theoretical value)=903, eluting time: 32.2 min.

WORKING EXAMPLE 6

Production of Hexamethyleniminocarbonyl-Leu-D-Trp(COOMe)-D-Nle-D-Asp (3MeOPhp)

(I) Production of 3MeOPhp.HCl

To a solution of 1.12 ml of m-anisidine in 20 ml of chlorobenzene was added 2.68 g of bis(2-chloroethyl) amine hydrochloride, and the mixture was refluxed overnight. The reaction mixture was concentrated, which was purified by means of a silica gel column Chromatography (eluent: 5% $CH_3OH$/DCM), followed by dissolving in 4N-HCl/ethyl acetate. To the solution was added ether to precipitate out the title compound, which was then collected by filtration. Yield: 2.09 g (91%), m.p.143–144° C., Rf1: 0.04 Rf2: 0.22

(II) Production of hexamethyleniminocarbonyl-Leu-D-Trp (COOMe)-D-Nle-D-Asp (3MeOPhp)-OBzl In 10 ml of DMF was dissolved 23 mg of 3MeOPhp.HCl produced in Working Example 6(I). To the solution were added 66 mg of hexamethyleniminocarbonyl-Leu-D-Trp (COOMe)-D-Nle-D-Asp-OBzl, 43 mg of HOBt, 31 mg of WSCD.HCl and 22 µl of TEA. The mixture was stirred overnight at room temperature. The reaction mixture was concentrated, which was dissolved in ethyl acetate. The solution was washed with 1N HCl and a 4% aqueous solution of $NaHCO_3$, which was further washed with water, followed by drying over $Na_2SO_4$ and concentration. To the concentrate was added ether to precipitate out the title compound, which was collected by filtration. Yield: 78 mg (79%), Rf1: 0.46 Rf2: 0.61

(III) Production of hexamethyleniminocarbonyl-Leu-D-Trp (COOMe)-D-Nle-D-Asp (3MeOPhp)

In 10 ml of DMF was dissolved 50 mg of hexamethyleniminocarbonyl-Leu-D-Trp(COOMe)-D-Nle-D-Asp (3MeOPhp)-OBzl produced in Working Example 6 (II). The solution was subjected to catalytic reduction for 3 hours in hydrogen streams using Pd black as the catalyst. The catalyst was filtered off, and the filtrate was dissolved in a small volume of acetic acid. To the solution was added water, which was freeze-dried, followed by purification by means of HPLC using a column D-ODS-5-ST(2 cm×15 cm) manufactured by YMC Inc. to afford hexamethyleniminocarbonyl-Leu-D-Trp(COOMe)-D-Nle-D-Asp (3MeOPhp). Yield: 7.7 mg (34%), MS: (M+H+)=903 (theoretical value)=903, eluting time: 33.8 minutes

WORKING EXAMPLE 7

Production of Hexamethyleniminocarbonyl-Leu-D-Trp(COOMe)-D-Nle-D-Asp(2MeO-5MePhp)

(I) Production of 2MeO-5MePhp.HCl

To the solution of 1.37 g of 2-methoxy-5-methylaniline in 20 ml of chlorobenzene was added 2.68 g of bis(2-chloroethyl)amine.HCl. The mixture was refluxed overnight. The reaction mixture was concentrated, which was purified by means of a silica gel column chromatography (eluent: 5% $CH_3OH/DCM$), followed by dissolving in 10 ml of 4N-HCl/ethyl acetate. The solution was concentrated, to which was added ether to precipitate out the title compound. The precipitate was collected by filtration. Yield: 1.73 g (71%), m.p.193–195° C. Rf1: 0.09 Rf2: 0.29

(II) Production of hexamethyleniminocarbonyl-Leu-D-Trp(COOMe)-D-Nle-D-Asp(2MeO-5MePhp)-OBzl In 10 ml of DMF was dissolved 24 mg of 2MeO-5MePhp.HCl. To the solution were added 66 mg of hexamethyleniminocarbonyl-Leu-D-Trp(COOMe)-D-Nle-D-Asp-OBzl produced in Working Example 5 (II), 43 mg of HOBt, 31 mg of WSCD.HCl and 22 μl of TEA. The mixture was stirred overnight at room temperature. The reaction mixture was concentrated, which was dissolved in ethyl acetate. The solution was sequentially washed with 1N HCl and a 4% aqueous solution of $NaHCO_3$, which was then further washed with water, followed by drying over $Na_2SO_4$ and concentration. To the concentrate was added ether to precipitate out the title compound, which was collected by filtration. Yield: 70 mg (70%), Rf1: 0.45 Rf2: 0.60

(III) Production of hexamethyleniminocarbonyl-Leu-D-Trp(COOMe)-D-Nle-D-Asp (2MeO-5MePhp)

In 10 ml of DMF was dissolved 50 mg of hexamethyleniminocarbonyl-Leu-D-Trp(COOMe)-D-Nle-D-Asp (2MeO-5MePhp)-OBzl. The solution was subjected to catalytic reduction for 3 hours in hydrogen streams using Pd black as the catalyst. From the reaction mixture, the catalyst was filtered off. The filtrate was dissolved in a small volume of acetic acid, to which was added water, followed by freeze-drying. The freeze-dried product was purified by means of HPLC using a column D-ODS-5-ST(2 cm×15 cm) manufactured by YMC Inc. to afford hexamethyleniminocarbonyl-Leu-D-Trp(COOMe)-Nle-D-Asp (2MeO-5MePhp). Yield: 2.7 mg (12%), MS: (M+H+)= 918 (theoretical value)=918, eluting time: 32.6 minutes

WORKING EXAMPLE 8

Production of Hexamethyleniminocarbonyl-Leu-D-Trp(COOMe)-D-Nle-D-Asp (2FPhp)

(I) Production of 2FPhp.HCl

To the solution of 966 μl of 2-fluoroaniline in 20 ml of chlorobenzene was added 2.68 g of bis(2-chloroethyl)amine.HCl, and the mixture was refluxed overnight. The reaction mixture was concentrated, which was purified by means of a silica gel column chromatography (eluent: 5% $CH_3OH/DCM$), followed by dissolving in 10 ml of ethyl acetate. To the solution was added ether to precipitate out the title compound, which was collected by filtration. Yield: 1.44 g (67%), m.p.148–150° C., Rf1: 0.05 Rf2: 0.23

(II) Production of hexamethyleniminocarbonyl-Leu-D-Trp(COOMe)-D-Nle-D-Asp (2FPhp)-OBzl In 10 ml of DMF was dissolved 20 mg of 2FPhp.HCl produced in Working Example 8(I). To the solution were added 66 mg of hexamethyleniminocarbonyl-Leu-D-Trp(COOMe)-D-Nle-D-Asp-OBzl, 43 mg of HOBt, 31 mg of WSCD.HCl and 22 μl of TEA. The mixture was stirred overnight at room temperature. The reaction mixture was concentrated, which was dissolved in ethyl acetate. The solution was sequentially washed with 1N HCl and a 4% aqueous solution of $NaHCO_3$, which was further washed with water, followed by drying over $Na_2SO_4$ and concentration. To the concentrate was added ether to precipitate out the title product, which was collected by filtration. Yield: 66 mg (67%), Rf1: 0.46 Rf2: 0.61

(III) Production of hexamethyleniminocarbonyl-Leu-D-Trp(COOMe)-D-Nle-D-Asp (2FPhp)

In 10 ml of DMF was dissolved 50 mg of hexamethyleniminocarbonyl-Leu-D-Trp(COOMe)-D-Nle-D-Asp (2FPhp)-OBzl produced in Working Example 8 (II). The solution was subjected to catalytic reduction for 3 hours in hydrogen streams using Pd black as the catalyst. The catalyst was filtered off, and the filtrate was dissolved in a small volume of acetic acid. To the solution was added water, which was freeze-dried. The freeze-dried product was purified by means of HPLC using a column D-ODS-5-ST(2 cm×15 cm) manufactured by YMC to afford hexamethyleniminocarbonyl-Leu-D-Trp(COOMe)-D-Nle-D-Asp (2FPhp). Yield: 1.9 mg (9%), MS: (M+H+)=891 (theoretical value)=891, eluting time: 35.3 minutes

WORKING EXAMPLE 9

Production of Hexamethyleniminocarbonyl-Ile-D-Trp(COOMe)-D-Nle-D-Asp(Php)

(I) Production of hexamethyleniminocarbonyl-Ile-OBzl

To a suspension of 118 mg of Ile-OBzl.p-Tos in 10 ml of THF were added 44 μl of TEA and 51 mg of CDI. The mixture was stirred for 1.5 hour under ice-cooling, to which was then added 41 μl of hexamethylenimine at room temperature. The mixture was stirred overnight at room temperature. The reaction mixture was concentrated, which was dissolved in ethyl acetate. The solution was sequentially washed with 1N HCl and a 4% aqueous solution of $NaHCO_3$, which was further washed with water, followed by drying and concentration. To the concentrate was added ether-petroleum ether to precipitate out the title compound, which was collected by filtration. Yield: 102 mg (98%), Rf1: 0.64 Rf2: 0.79

(II) Production of hexamethyleniminocarbonyl-Ile-D-Trp(COOMe)-D-Nle-D-Asp(Php)

In 10 ml of MeOH was dissolved 69 mg of hexamethyleniminocarbonyl-Ile-OBzl produced in Working Example 9 (I). The solution was subjected to catalytic reduction for 3 hours in hydrogen streams using Pd black as the catalyst. The catalyst was filtered off, and the reaction mixture was concentrated to give hexamethyleniminocarbonyl-Ile, which was subjected to substantially the same procedure as in Working Example 2 to give hexamethyleniminocarbonyl-Trp(COOMe)-D-Nle-D-Asp(Php)-OBzl. Fifty mg of this compound was dissolved in 10 ml of DMF. The solution was subjected to catalytic reduction for 3 hours in hydrogen streams using Pd black as the catalyst. The catalyst was filtered off, and the filtrate was dissolved in a small volume of acetic acid. To the solution was added water, which was freeze-dried. The freeze-dried product was purified by means of HPLC using a column D-ODS-5-ST(2 cm×15 cm) manufactured by YMC Inc. to afford hexamethyleniminocarbonyl-Ile-D-Trp(COOMe)-D-Nle-D-Asp(Php). Yield: 6.9 mg (31%), MS: (M+H+)=873 (theoretical value)=873, eluting time: 33.0 minutes.

WORKING EXAMPLE 10

Production of Hexamethyleniminocarbonyl-Nle-D-Trp(COOMe)-D-Nle-D-Asp(Php)

(I) Production of hexamethyleniminocarbonyl-Nle-$OCH_3$

To the suspension of 335 mg of Nle-$OCH_3$.HCl in 15 ml of THF were added 294 μl of TEA and 341 mg of CDI. The mixture was stirred for one hour under ice-cooling, to which was then added 270 μl of hexamethylenimine. The mixture was stirred overnight at room temperature. The reaction mixture was concentrated, which was dissolved in ethyl acetate. This solution was sequentially washed with 1N HCl and a 4% aqueous solution of $NaHCO_3$, followed by drying over $Na_2SO_4$ and concentration. To the concentrate was added ether-petroleum ether to precipitate out the title compound, which was collected by filtration. Yield: 196 mg (36%), m.p.60–61° C., Rf1: 0.48 Rf2: 0.65

(II) Production of hexamethyleniminocarbonyl-Nle-D-Trp(COOMe)-D-Nle-D-Asp(Php)

In 10 ml of MeOH was dissolved 135 mg of hexamethylenminocarbonyl-Nle-$OCH_3$ produced in Working Example 10 (I). To the solution was added, under ice-cooling, 5 ml of 1N-NaOH, and the mixture was stirred for 1.5 hour at room temperature. To the reaction mixture was then added, under ice-cooling, 4.5 ml of 1N HCl, which was concentrated. The concentrate was dissolved in ethyl acetate. This solution was washed with 1N HCl, which was further washed with water, followed by drying over $Na_2SO_4$ and concentration to give hexamethyleniminocarbonyl-Nle-D-Trp(COOMe)-D-Nle-D-Asp(Php)-OBzl. In 10 ml of DMF was dissolved 44 mg of this compound. The solution was subjected to catalytic reduction for 3 hours in hydrogen streams using Pd black as the catalyst. From the reaction mixture, the catalyst was filtered off. The filtrate was dissolved in a small volume of acetic acid, to which was added water, followed by freeze-drying. The freeze-dried product was purified by means of HPLC using a column D-ODS-5-ST(2 cm×15 cm) manufactured by YMC Inc. to afford hexamethyleniminocarbonyl-Nle-D-Trp(COOMe)-D-Nle-D-Asp(Php). Yield: 7.8 mg (36%), MS: (M+H+)=873 (theoretical value)=873, eluting time: 33.4 minutes

WORKING EXAMPLE 11

Production of Hexamethyleniminocarbonyl-Leu-D-Trp(COOMe)-D-Nle-Atp-2MeOPhp (I) Production of Boc-D-Asp(2MeOPhp)-OBzl A solution of 10.06 g of 1-(2-methoxyphenyl) piperazine hydrochloride in 40 ml of DMF was ice-cooled. To the solution was added an acetonitrile solution of Boc-D-Asp(ONB)-OBzl prepared from 12.93 g of Boc-D-Asp-OBzl, 7.88 g of HONB and 8.41 g of WSCD.HCl. The mixture was stirred overnight at room temperature, The reaction mixture was concentrated, which was dissolved in ethyl acetate. The solution was sequentially washed with 1N HCl and a 4% aqueous solution of $NaHCO_3$, which was further washed with water, followed by drying and concentration to afford the title compound. Yield: 18.48 g (93%) $Rf_1$: 0.77 $Rf_2$: 0.83 MS: (M+H+)=498 (theoretical value)=498

(II) Production of Z-D-Asp(2MeOPhp)—$NH_2$

A solution of 4.39 g of Boc-D-Asp(2MeOPhp)-OBzl produced in the above (I) in 30 ml of 4N-HCl/ethyl acetate was stirred for 30 minutes under ice-cooling. The reaction mixture was concentrated, to which was added ether to precipitate out the product. The precipitate was recovered by filtration and dried, which was dissolved in 30 ml of DMF. The solution was ice-cooled, to which were added 3.08 ml of TEA and 1.45 ml of Z-Cl. The mixture was stirred for 5 hours at room temperature. The reaction mixture was concentrated, which was dissolved in ethyl acetate. The solution was washed sequentially with 1N HCl and a 4% aqueous solution of $NaHCO_3$, which was further washed with water, followed by drying over $Na_2SO_4$ and concentration. The concentrate was dissolved in 60 ml of methanol, to which was added, under ice-cooling, 30 ml of a 1N aqueous solution of sodium hydroxide. The mixture was stirred for one hour at room temperature. To the reaction mixture was added, under ice-cooling, 21.2 ml of 1N HCl to adjust the pH to 7, followed by concentration under reduced pressure. The concentrate was dissolved in a mixture of ethyl acetate and 1N HCl. The mixture was shaken and left standing to separate into two layers. The organic layer was washed with a 4% aqueous solution of $NaHCO_3$, which was further washed with water, followed by drying over $Na_2SO_4$, followed by concentration. To the concentrate was added ether-petroleum ether to precipitate out the title compound, which was collected by filtration. Yield: 2.71 g (77%) $Rf_1$: 0.32 $Rf_2$: 0.62 MS: (M+H+)=441 (theoretical value)=441

(III) Z-Acp-2MeOPhp

In 4 ml of pyridine was dissolved 1.76 g of Z-D-Asp(2MeOPhp)—$NH_2$ produced in the above (II). The solution was stirred for 10 minutes at temperatures not higher than −5° C. To the reaction mixture were added 0.56 ml of phosphorus oxychloride and 1 ml of dichloromethane. The mixture was stirred for one hour at 0° C. or below. The reaction mixture was concentrated, which was dissolved in ethyl acetate. The solution was washed sequentially with 1N HCl and a 4% aqueous solution of $NaHCO_3$, which was further washed with water, followed by drying over $Na_2SO_4$ and concentration. To the concentrate was added ether-petroleum ether to precipitate out the product, which was collected by filtration. Yield: 1.39 g (66%) $Rf_1$: 0.49 $Rf_2$: 0.68 MS: (M+H+)=423 (theoretical value)=423

(IV) Production of Z-Atp-2MeOPhp

In 5 ml of xylene was dissolved 211 mg of Z-Acp-2MeOPhp produced in the above (III). To the solution were added 407 μl of tributyltin chloride and 98 mg of sodium azide. The mixture was heated for 18 hours under reflux. The reaction mixture was cooled, to which was added 20 ml of 2N HCl, followed by washing with ether. To the solution was added, under ice-cooling, a 1N aqueous solution of sodium hydroxide to adjust the pH to 5, which was subjected to extraction with dichloromethane three times. The extract solution was washed with water, dried over $Na_2SO_4$ and concentrated to afford the object product. Yield: 91 mg (39%) $Rf_1$: 0.08 $Rf_2$: 0.62 MS: (M+H+)=466 (theoretical value)=466

(V) Production of hexamethyleniminocarbonyl-Leu-D-Trp(COOMe)-D-Nle-Atp-2MeOPhp

Using Z-Atp-2MeOPhp produced in the above (IV), a peptide chain was elongated in substantially the same manner as in Working Example 1 (II) (in this Working Example, TEA was not employed). The product was purified by means of HPLC using a column D-ODS-5-ST(2 cm×15 cm) manufactured by YMC Inc to afford hexamethyleniminocarbonyl-Leu-D-Trp(COOMe)-D-Nle-Atp-2MeOPhp. Yield: 1.9 mg LSIMS: (M+H+)=928 (theoretical value)=928 eluting time 33.0 minutes A peptide derivative of compound No. 12 in the following Table 1 can be also produced by using Boc-Asp(OBl) instead of Boc-D-Asp-OBzl in the producing process of working example 11. The above-mentioned compounds are shown in Table 1. In Table 1, an asterisk mark indicates the configuration of asymmetric carbon atom.

TABLE 1
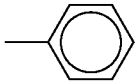
| Cpd. No. | A₁ | R¹⁴ | n¹ | n² | R¹⁵ | R¹⁶ | * |
|---|---|---|---|---|---|---|---|
| 1 | Leu | CHO | 0 | 1 | 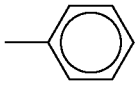 | COOH | R |
| 2 | Leu | COOCH₃ | 0 | 1 | 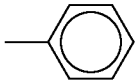 | COOH | R |
| 3 | Leu | COOCH₃ | 0 | 1 | 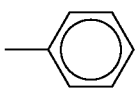 | COOH | S |
| 4 | Leu | COOCH₃ | 2 | 0 | 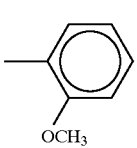 | COOH | R |
| 5 | Leu | COOCH₃ | 0 | 1 | 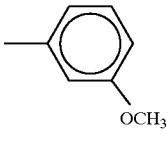 | COOH | R |
| 6 | Leu | COOCH₃ | 0 | 1 | 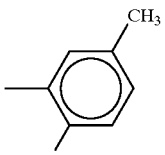 | COOH | R |
| 7 | Leu | COOCH₃ | 0 | 1 | 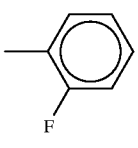 | COOH | R |
| 8 | Leu | COOCH₃ | 0 | 1 | 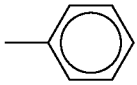 | COOH | R |
| 9 | Ile | COOCH₃ | 0 | 1 |  | COOH | R |

TABLE 1-continued

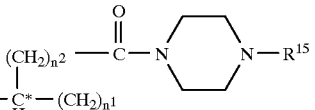

| Cpd. No. | A₁ | R¹⁴ | n¹ | n² | R¹⁵ | R¹⁶ | * |
|---|---|---|---|---|---|---|---|
| 10 | Nle | COOCH₃ | 0 | 1 | 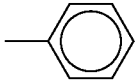 | COOH | R |
| 11 | Leu | COOCH₃ | 0 | 1 | 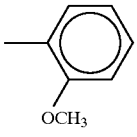 | 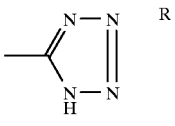 | R |
| 12 | Leu | COOCH₃ | 1 | 0 | 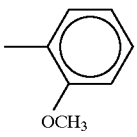 | 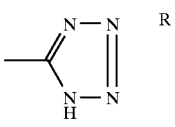 | R |

Formulation Example 1

In 50 ml of distilled water for injection (JP) was dissolved 50 mg of the compound produced in Working Example 5. To the solution was added distilled water for injection (JP) to make the whole volume 100 ml. This solution was subjected to filtration under sterile conditions. A one ml portion of this solution was filled in a vial for injection under sterile conditions, which was lyophilized and closed tightly.

Formulation Example 2

In 50 ml of distilled water for injection (JP) was dissolved 0.5 g of monohydrochloride of the compound produced in Working Example 5. To the solution was added distilled water for injection (JP) to make the whole volume 100 ml. This solution was subjected to filtration under sterile conditions. A one ml each portion of this solution was filled in a vial for injection under sterile conditions, which was lyophilized and closed tightly.

Test Example 1

The membrane fraction of CHO cells on which human endothelin receptor ($ET_A$ or $ET_B$) was expressed was diluted to 0.15 mg/ml with an assaying buffer and dispensed to assaying tubes at 100 μl per tube. To this membrane fraction suspension were added 2 μl of a solution of endothelin-1 labeled with radioactive iodine (5 nM) and 3 μl of a 50% dimethyl sulfoxide of the test compound, followed by incubation at 25° C. for one hour. The membrane fraction suspension was diluted with 900 μl of an ice-cooled assaying buffer and centrifuged at 12,000×G for 10 minutes to separate supernatant and precipitate. The precipitate contained cell membranes and endothelin receptors embedded therein. The receptor-bound endothelin, labeled with radioactive iodine, was also recovered in the precipitate. The radioactive iodine in this precipitate was counted, using a gamma ray counter, to determine the amount of radioactive-iodine-labeled endothelin-1 bound to the endothelin receptors. The results of the quantitative determination were shown in the respective $IC_{50}$(nm) values in the following Table 2.

TABLE 2

| Compound | $IC_{50}$ (nM) | |
|---|---|---|
| W. Ex. No. | $ET_A$ | $ET_B$ |
| 1 | 1.8 | 130 |
| 2 | 11 | 18 |
| 3 | 45 | 34 |
| 4 | 23 | 23 |
| 5 | 7.1 | 7.9 |
| 6 | 28 | 29 |
| 7 | 49 | 110 |
| 8 | 18 | 29 |
| 9 | 21 | 15 |
| 10 | 34 | 75 |

Test Example 2

A) From the coronary arteries isolated from porcine hearts, ring samples of 3 mm width were prepared. These samples were suspended in a Magnus tubes filled with Krebs solution, which were equilibrated at a passive tension of 2 g for 1.5 hour. These samples were subjected to constriction with KCl (60 mM) for 10 minutes to give maximum reaction and, then, washed, followed by leaving stably for one hour. The samples or vehicles were pre-treated for 30 minutes, followed by addition of endothelin-1 3 nM to observe the maximum constriction. Assuming the KCl constriction in each sample as 100%, the constriction rate (% KCl) of endothelin-1 was calculated. From the inhibition rate of test compound groups when the constriction rate of the vehicle groups was assumed as 100%, the inhibition rate was calculated.

B) Using coronary vein isolated from porcine hearts, the constriction inhibition rate was calculated in substantially the same manner as in A) above employing Sarafotoxin S6C [Sarafotoxin S6C: C. Takasaki et al., Toxicon, 26, 543 (1988)] (1 nM) at a passive tension of 0.5 g.

The results obtained in A) and B) were shown in the following Table 3 as % inhibition.

TABLE 3

| | | |
|---|---|---|
| Compound of W. Ex. 5 | 1 μM | A) 72.7 + 10.5% (n = 4) |
| Compound of W. Ex. 5 | 0.1 μM | B) 91.6 + 2.9% (n = 4) |

We claim:

1. A peptide derivative represented by the formula $R^{1'}$–CO—$A_1$—$A_2$—$A_3$—$A_4$, wherein $R^{1'}$ is an optionally substituted N-containing saturated heterocyclic group which is bonded to the —CO— group at the ring-constituting nitrogen atom, $A_1$ is Leu, Ile or Nle, $A_2$ is an optionally substituted D-Trp, $A_3$ is D-Leu, D-Ile or D-Nle, and $A_4$ is Asp, Glu, tetrazolyl-α-Ala or tetrazolyl-β-Ala having a first carboxyl group which is amidated with an optionally substituted first heterocyclic group, wherein the first heterocyclic group is selected from the group consisting of hexamethylenimino, 10,11-dihydro-5H-dibenz(b,f)azepin-5-yl, 4-morpholinyl, 1-piperazinyl and azepinyl, and having a second carboxyl group or a second heterocyclic group capable of releasing a proton, or a salt thereof.

2. The peptide derivative as claimed in claim 1, wherein a hydrogen atom on a carbon atom of $A_4$ is substituted with the second carboxyl group or the second heterocyclic group capable of releasing a proton, or a salt thereof.

3. The peptide derivative as claimed in claim 1, consisting of 4 to 6 amino acid residues.

4. The peptide derivative as claimed in claim 1, wherein the second heterocyclic group capable of releasing a proton is a 4- to 6-membered heterocyclic group having 1 to 4 nitrogen atoms, oxygen atoms and/or sulfur atoms, and optionally having a hydroxy or oxo group as the substituent, or the heterocyclic group is condensed with a benzene ring.

5. The peptide derivative as claimed in claim 1, wherein the substituent of the optionally substituted first heterocyclic group is a $C_{1-6}$ alkyl group, an optionally substituted $C_{6-14}$ aryl group, a N-containing 5- to 6-membered heterocyclic group, a halogen atom, nitro, cyano, hydroxy, a $C_{1-6}$ alkoxy group, amino, oxo, amidino, imino, mercapto, sulfo, a mono- or di-$C_{1-6}$ alkylamino, formylamino, a $C_{1-6}$ alkylsulfonylamino group, a $C_{1-6}$ alkoxycarbonyl group, carboxyl, formyl, a $C_{1-6}$ alkylcarbonyl group, a $C_{2-6}$ alkenyl group, a $C_{2-6}$ alkynyl group, a $C_{3-9}$ cycloalkyl group, a $C_{5-7}$ cycloalkenyl group, a $C_{7-13}$ aralkyl group, a $C_{1-6}$ alkylthio group, a $C_{1-6}$ alkylsulfinyl group, a $C_{1-6}$ alkylsulfonyl group, or a group of the formula: $R^9$—CO—$X^3$—, wherein $R^9$ is a $C_{1-6}$ alkyl group, a $C_{1-6}$ alkoxy group, or an amino group which may optionally be substituted with $C_{1-6}$ alkyl, and $X_3$ is an oxygen atom or a group of the formula: —$NR^{10}$—, wherein $R^{10}$ is a hydrogen atom or a $C_{1-6}$ alkyl group.

6. The peptide derivative as claimed in claim 1, which consists of 4 amino acid residues.

7. The peptide derivative as claimed in claim 1, wherein Asp or Glu is of the D-configuration.

8. The peptide derivative as claimed in claim 1, wherein the substituent of the optionally substituted N-containing saturated heterocyclic group for $R^{1'}$ is a $C_{1-6}$ alkyl group, phenyl, a halogen atom, nitro, cyano, hydroxy, oxo, a $C_{1-6}$ alkoxy group, amino or a mono- or di-$C_{1-6}$ alkylamino group.

9. The peptide derivative as claimed in claim 1, wherein the substituent of D-Trp is a $C_{1-6}$ alkyl group, a $C_{1-6}$ alkoxy group, a $C_{1-6}$ alkoxy-carbonyl group, a $C_{1-6}$ acyl group, cyano, a halogen atom, hydroxy, a hydroxy-$C_{1-6}$ alkyl group or a group of the formula: —$S(O)_a$—$R^{21}$, wherein a is an integer of 0 to 2, and $R^{21}$ is a $C_{1-6}$ alkyl group.

10. The peptide derivative as claimed in claim 1, wherein the substituent of the first heterocyclic group for $A_4$ is a $C_{6-14}$ aryl group.

11. The peptide derivative as claimed in claim 1, which is hexamethyleniminocarbonyl-Leu-D-Trp(COOMe)-D-Nle-D-Asp (2MeOPhp).

12. The peptide derivative as claimed in claim 1, which is hexamethyleniminocarbonyl-Leu-D-Trp(COOMe)-D-Nle-Atp-2MeOPhp.

13. A pharmaceutical composition containing the peptide derivative as claimed in claim 1, or a pharmaceutically acceptable salt thereof, together with a pharmaceutically acceptable carrier or diluent.

14. The pharmaceutical composition as claimed in claim 13, which is an endothelin receptor antagonist.

15. The pharmaceutical composition as claimed in claim 14, in which the endothelin receptor antagonist is a therapeutic or prophylactic agent of cardio- or cerebro-circulatory disease, hepatic disease and/or renal disease.

16. The pharmaceutical composition as claimed in claim 14, in which the endothelin receptor antagonist is a vasoconstriction inhibitor of cardio- or cerebro-vascular disease, hepatic vascular and/or renal vascular.

17. The pharmaceutical composition as claimed in claim 14, in which the endothelin receptor antagonist is a therapeutic and prophylactic agent of acute renal failure, myocardial infarction, and/or bronchial disorder.

18. A method for treating a mammal suffering from acute renal failure, comprising administering an effective amount of the pharmaceutical composition of claim 13 to a mammal in need thereof.

19. A method for treating a mammal suffering from myocardial infarction, comprising administering an effective amount of the pharmaceutical composition of claim 13 to a mammal in need thereof.

20. A method for treating a mammal suffering from bronchial disease, comprising administering an effective amount of the pharmaceutical composition of claim 13 to a mammal in need thereof.

21. A method for treating a mammal suffering from vasoconstriction, which comprises administering an effective amount of the pharmaceutical composition of claim 13 to a mammal in need thereof.

22. A method of producing a peptide derivative according to claim 1 or a salt thereof, which method comprises subjecting a peptide derivative comprising a peptide having the formula $R^{1'}$—CO—$A_1$—$A_2$—$A_3$—$A_4$, wherein $R^1$ is an optionally substituted N-containing saturated heterocyclic group which is bonded to the —CO— group at the ring-constituting nitrogen atom, $A_1$ is Leu, Ile or Nle, $A_2$ is an optionally substituted D-Trp, $A_3$ is D-Leu, D-Ile or D-Nle, and $A_4$ is Asp, Glu, tetrazolyl-α-Ala or tetrazolyl-β-Ala having a first carboxyl group which is amidated with an optionally substituted first heterocyclic group, wherein the first heterocyclic group is selected from the group consisting of hexamethylenimino, 10,11-dihydro-5H-dibenz(b,f) azepin-5-yl, 4-morpholinyl, 1-piperazinyl and azepinyl, and having a second carboxyl group which is protected by a protective group, to an elimination reaction of the protective group.

23. A method of producing a peptide derivative according to claim 1 or a salt thereof, which method comprises subjecting a peptide derivative comprising a peptide having the formula $R^{1'}$—CO—$A_1$—$A_2$—$A_3$—$A_4$, wherein $R^{1'}$ is an optionally substituted N-containing saturated heterocyclic group which is bonded to the —CO— group at the ring-constituting nitrogen atom, $A_1$ is Leu, Ile or Nle, $A_2$ is an optionally substituted D-Trp, $A_3$ is D-Leu, D-Ile or D-Nle, and $A_4$ is Asp, Glu, tetrazolyl-α-Ala or tetrazolyl-β-Ala having a first carboxyl group which is amidated with an optionally substituted first heterocyclic group, wherein the first heterocyclic group is selected from the group consisting of hexamethylenimino, 10,11-dihydro-5H-dibenz(b,f)azepin-5-yl, 4-morpholinyl, 1-piperazinyl and azepinyl, and having a second heterocyclic group capable of releasing a proton, to a condensation reaction.

* * * * *